(12) United States Patent
MacKay et al.

(10) Patent No.: US 12,340,175 B2
(45) Date of Patent: Jun. 24, 2025

(54) AUTOMATED CLASSIFICATION OF EMOTIO-COGNITON

(71) Applicant: ELABORATION, INC., Santa Cruz, CA (US)

(72) Inventors: Joy MacKay, Ignacio, CA (US); Anthony Davis, Ashland, OR (US)

(73) Assignee: ELABORATION, INC., Santa Cruz, CA (US)

( * ) Notice: Subject to any disclaimer, the term of this patent is extended or adjusted under 35 U.S.C. 154(b) by 357 days.

(21) Appl. No.: 17/589,512

(22) Filed: Jan. 31, 2022

(65) Prior Publication Data

US 2022/0245354 A1 Aug. 4, 2022

Related U.S. Application Data

(60) Provisional application No. 63/163,618, filed on Mar. 19, 2021, provisional application No. 63/163,621, (Continued)

(51) Int. Cl.
*G06F 40/30* (2020.01)
*G06F 3/0488* (2022.01)
(Continued)

(52) U.S. Cl.
CPC .......... *G06F 40/30* (2020.01); *G06F 3/0488* (2013.01); *G06F 40/169* (2020.01); (Continued)

(58) Field of Classification Search
CPC ...... G06F 40/30; G06F 40/216; G06F 40/284; G06F 40/268
See application file for complete search history.

(56) References Cited

U.S. PATENT DOCUMENTS 8,200,477 B2* 6/2012 Yi ................ G06F 40/242
707/939
9,965,443 B2* 5/2018 Eggink ............ G06F 40/10
(Continued)

FOREIGN PATENT DOCUMENTS

EP 3 392 884 A1 10/2018

OTHER PUBLICATIONS

Eyal Shnarch, et al., "GrASP: Rich Patterns for Argumentation Mining", Proceedings of The 2017 Conference on Empirical Methods in Natural Language Processing, Sep. 7-11, 2017, pp. 1345-1350.
(Continued)

*Primary Examiner* — Samuel G Neway
(74) *Attorney, Agent, or Firm* — Ascenda Law Group, PC

(57) ABSTRACT

A system and method for detecting a psychological affect in a natural language content with a rule-based engine includes receiving the natural language content as a textual input; searching for matches between linguistic rules for a given emotio-cognition and components of the natural language content, wherein instances of the linguistic rules have human dimensions; activating the matched linguistic rules, and evaluating the human dimensions of the matched rules; scoring each human dimension to obtain a profile of dimension scores for the given emotio-cognition; aggregating the dimensions in the obtained profile of dimension scores to obtain an intensity indication for the given emotio-cognition; and displaying the natural language content in a manner that relates the matched linguistic rules in conjunction with the given emotio-cognition and respective intensity indication of the given emotio-cognition.

16 Claims, 27 Drawing Sheets

Related U.S. Application Data filed on Mar. 19, 2021, provisional application No. 63/162,987, filed on Mar. 18, 2021, provisional application No. 63/143,730, filed on Jan. 29, 2021.

(51) Int. Cl.

| | |
|---|---|
| *G06F 40/169* | (2020.01) |
| *G06F 40/216* | (2020.01) |
| *G06F 40/268* | (2020.01) |
| *G06F 40/284* | (2020.01) |
| *G06V 20/40* | (2022.01) |
| *G10L 15/18* | (2013.01) |
| *G10L 25/57* | (2013.01) |
| *G10L 25/63* | (2013.01) |
| *G16H 50/20* | (2018.01) |

(52) U.S. Cl.
CPC .......... *G06F 40/216* (2020.01); *G06F 40/268* (2020.01); *G06F 40/284* (2020.01); *G06V 20/41* (2022.01); *G10L 15/18* (2013.01); *G10L 25/57* (2013.01); *G10L 25/63* (2013.01); *G16H 50/20* (2018.01)

(56) References Cited

U.S. PATENT DOCUMENTS

| | | |
|---|---|---|
| 10,387,556 B2 | 8/2019 | Ekambaram et al. |
| 10,856,032 B2 | 12/2020 | Aimone et al. |
| 10,896,428 B1 | 1/2021 | Bajasnbramaniam et al. |
| 2010/0023311 A1* | 1/2010 | Subrahmanian ...... G06F 16/345 707/E17.109 |
| 2013/0311485 A1* | 11/2013 | Khan .................... G06F 16/335 707/758 |
| 2015/0318002 A1 | 11/2015 | Karam et al. |
| 2016/0042359 A1* | 2/2016 | Singh ...................... G06F 40/30 704/2 |
| 2017/0008351 A1 | 1/2017 | Kodama |
| 2019/0179900 A1* | 6/2019 | Wang ..................... G06F 40/289 |
| 2019/0215290 A1* | 7/2019 | Kozloski ................. H04L 51/42 |
| 2020/0184345 A1* | 6/2020 | Jyoti ........................ G06N 5/02 |
| 2022/0245354 A1* | 8/2022 | Mackay .................. G10L 25/57 |

OTHER PUBLICATIONS

Md Shad Akhtar, et al., "How Intense Are You? Predicting Intensities of Emotions and Sentiments Using Stacked Ensemble", Application Notes, IEEE Computational Intelligence Magazine, vol. 15, No. 1, Feb. 2020, pp. 64-75.

International Search Report and Written Opinion issued Nov. 3, 2022, in PCT/US22/20994, 18 pages.

Algerian Office Action issued Jan. 28, 2024 in Algerian Patent Application No. 231464, 1 page.

Alswaidan; et al., "A survey of state-of-the-art approaches for emotion recognition in text", Knowledge and Information Systems (2020), Mar. 18, 2020, 62(8):2937-2987.

Fares; et al., "Difficulties and Improvements to Graph-based Lexical Sentiment Analysis using LISA", 2019 IEEE International Conference on Cognitive Computing (ICCC), Jul. 8, 2019, pp. 28-35.

Extended European Search Report dated May 12, 2025, from the European Patent Office, for EP Patent Application No. 22760594.6, 13 pgs.

* cited by examiner o Utilizing Part-of-Speech Tagging/Syntax: ← 602
IF contains NNP followed by a VP
...

o Exact String: ← 604
IF contains "That sounds super!"
...

o Token proximity: ← 606
IF contains "Family" within 8 words of "happy"
...

o Punctuation: ← 608
IF number of exclamation points> 1
← 610
o Utilizing Lemmatization:
  IF contains words with the lemma "good" (good, better, best)
  ... ← 612 o Utilizing Stemming:
IF contains words with the stem "run" (running, ran, run)
... ← 614 o Lexicon:
  IF contains words present in a given lexicon, with associated scores
  ← 616
o Word Lookups/ Dictionaries:
  IF contains words present in a dedicated word list

A written fiction or nonfiction work is assessed for emotional, cognitive, interpersonal or social dynamic, motivation, belief, opinion, or psychological elements, assessed by a rule-based engine.

S1704

Text is scanned and tagged with rules that triggers, emotional, cognitive or otherwise states that are identified, and the intensity with which they have occurred.

S1706

Optional heat maps are generated within the text, displaying colors designated for occurrence of certain emotional or cognitive or sociological or interpersonal dynamics or states.

S1708

Optional sidebars summarizing the emotional, psychological, cognitive, sociological, or interpersonal dynamics or states occur to the right, with added context where available and/or necessary.

S1710

Each state can be interacted with by selecting (via touch, mouse, keyboard, etc.) allowing the reader to be presented with a list of examples within the text of that given state.

FIG. 17

S2302
A scene from a movie or television show or streaming show or captured theatre play or animated video source receives coordinated textual transcription from a module.

S2304
Textual data is mined by a rule-based engine, which tags emotional, cognitive, and other such states, with intensity ratings, throughout the transcription.

S2306
Contextual clues are provided by word coocurrence, discursive elements, and topic elements.

S2308
Individual strings or n-grams are also optionally marked with trinary dimensional scores.

S2310
Further information (FI) and situational elements (SE) apparent in visual data or tone elements apparent in auditory data are entered into a separate, but time-coordinated, source for the media.

S2312
Juxtaposition (coordination and divergence, and degree of each) from the contextual clues and FI and SE data occurs, creating Context Scores for each scene.

S2314
Bracketed emotional data is returned inline and inserted into the transcript for the benefit of the viewer watching the show, so that they may have an easier time correctly identifying emotional, cognitive or social elements of the media.

FIG. 23

AUTOMATED CLASSIFICATION OF EMOTIO-COGNITON

CROSS-REFERENCE TO RELATED APPLICATIONS

This application claims the benefit of priority to provisional application No. 63/143,730 filed Jan. 29, 2021, the entire contents of which are incorporated herein by reference.

This application claims the benefit of priority to provisional application No. 63/162,987 filed Mar. 18, 2021, the entire contents of which are incorporated herein by reference.

This application claims the benefit of priority to provisional application No. 63/163,618 filed Mar. 19, 2021, the entire contents of which are incorporated herein by reference.

This application claims the benefit of priority to provisional application No. 63/163,621 filed Mar. 19, 2021, the entire contents of which are incorporated herein by reference.

BACKGROUND

Field of the Invention

The present disclosure relates generally to monitoring affect, and in particular classifying and tracking intensity of emotio-cognition in natural language content.

Description of the Related Art

Affective computing is the study and development of systems and devices that can recognize, interpret, process, and simulate human affects. Affective computing is a multidisciplinary field that brings together linguistics, statistics, human factors and computer science. One aspect of affective computing is to enable bots and other computer applications to respond intelligently to natural human emotional feedback. In the case of text, affective computing includes emotion detection from text. More often, a form of emotion detection known as sentiment analysis is used to classify text as positive, negative, or neutral. Just about every major company that develops computer software and hardware, as well as university research, and several startups have development projects that include some form of tools for sentiment analysis. The popularity of sentiment analysis stems from the need to better understand sentiment in reactions to news media and various customer comments that are widespread in social media, customer product comments, and interactions with chat bots.

In practice, sentiment analysis is the use of natural language processing, text analysis, computational linguistics, and biometrics to systematically identify, extract, quantify, and study affective emotio-cognition states and subjective information. Sentiment analysis has been accelerated in part due to the availability of large data sets of human dialog, which are obtained from such sources as various social media platforms, recorded conversations, and other outlets for textual expression. However, sentiment analysis must deal with the evolving nature of natural language. For example, sentiment analysis must deal with subtle distinctions or variations in meaning between words, or even whole phrases. Some phrases may appear to indicate the same thought, but may indicate a difference in sentiment. Sentiment analysis must deal with words or phrases that may have different meanings depending on the context.

Despite significant recent advances in technologies used for natural language processing, sentiment analysis suffers from being tied to training sets, which typically have been manually classified, and is thereby subjective. In particular, annotation of big training datasets of text is performed manually. Training sets from manual classification methods tend to be slow, poor-performing, and expensive. Additionally, financially competitive methods of obtaining raters, primarily Mechanical Turk, suffer from non-native speakers incentivized to rush through classification tasks, resulting in low-quality, conflicting results, with attempts at prevention of these effects limited to cumbersome ID-scanning and unreliable IP-address filtering. Subtle emotion detection is difficult and error prone.

Moreover, training sets used for machine learning do not afford for creativity in language. Human beings have an apparent infinite ability to generate novel sentences through speech and writings, never before written or spoken. Indeed, a necessary property of language is precisely this allowance for such creativity, which current state of the art systems are unable to effectively accommodate.

State-of-the-art technology machine learning models for natural language processing (BERT (Bidirectional Encoder Representations from Transformers), GPT2 (Generative Pre-trained Transformer 2), GPT3), which are seemingly robust tools that can hold so much in memory and effectively look bi-directionally, are no match for an evolving natural language. Statistical models rely on strong statistical, often probabilistic components. Supervised machine learning models predict things they have seen before or relationships they've seen reoccur. There are countless phrases and sentences to be made in the future that cannot be encapsulated by sentences that have come before, including elements like portmanteaus, slang, jargon, metaphor or invented words.

In addition, there is still a semantic deficit in sentiment analysis; this is in part due to a lack of effective methods for measuring the intensity of emotions, the use of culled and unrepresentative datasets for training purposes. Additionally, overreliance of lexicon-centric or token-based solutions prevents such solutions from ultimately obtaining staying power, as linguists and engineers contend with the dynamic nature of language, including semantic shifts, obsolescence, and various other linguistic changes over time.

As such, sentiment analysis suffers from several major issues; namely, lack of gold-standard datasets with objectively rated or labeled data for training, limitations of n-gram based solutions, lack of the ability to determine bonafide intensity, difficulty parsing hashtags, and lack of rigorous validation for results. Additionally, while like-scale affective ratings are subjectively applied, no sound means exists within the industry or academia to validate classification results.

While the occasional attempt to quantify pragmatic factors (predominantly via brainstormed enumeration, and occasionally using n-gram selection with high token:type ratios) surfaces in the sociolinguistic literature, it is the study of sociolinguistics that largely focuses on fMRI studies, social or real-world experiments, intuitive analyses, and close examination and comparison of intuitive, pragmatic examples. Specific, but limited, syntactically-driven theories exist within the field, largely in individual constructions such as Andrews construction (adjectival and adverbial phrases with the construction "X knows," e.g., "God [only] knows," "Who knows") or somewhat more comprehensively, the semantically rich, complex but verb-centered seminal analysis of construction grammar, focused on specific grammatical constructions for object relationships, known as argument structure, dealing by nature with arguments (objects) of verbs.

Preferably, to be a construction, a piece of language has to be permutable and modular. By nature, this creates a focus not just on grammatical rules, but on common usage. Sociolinguistics have focused on pragmatics, the science of usage in the real world, analyzing specific word usage in a magnified view. However, analysis of constructions has been focused on argument structure, and verb-focused analysis of form-meaning pairings. There is a need for more efficient, robust and accurate detection of cognition, emotion, and emotio-cognition, which bridges cognitive science, social-linguistics and semantics.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

According to an embodiment of the present disclosure, an aspect is a method for detecting a psychological affect in a natural language content with a rule-based engine implemented by processing circuitry, the method can include receiving, via an input device, the natural language content as a textual input; preprocessing, by the processing circuitry, the natural language content; searching, by the rule-based engine, for matches between a plurality of linguistic rules for a given emotio-cognition and components of the preprocessed natural language content, wherein instances of the linguistic rules have one or more human dimensions; activating, by the rule-based engine, the matched linguistic rules, and evaluating the one or more human dimensions of the matched rules; scoring, by the rule-based engine, each human dimension to obtain a profile of dimension scores for the given emotio-cognition; aggregating, by the rule-based engine, the dimensions in the obtained profile of dimension scores to obtain an intensity indication for the given emotio-cognition; and displaying, by a display, the natural language content in a manner that relates the matched linguistic rules in conjunction with the given emotio-cognition and respective intensity indication of the given emotio-cognition.

Further, according to an embodiment of the present disclosure, a further aspect is an electronic reader, that can include a touchscreen display; processing circuitry; and a memory, wherein the touchscreen display is configured to display text of an electronic book; the processing circuitry is configured to implement a rule-based engine that scans and tags the text using rules that detect and trigger emotio-cognitive states, and determines intensity with which the emotio-cognitive states have occurred; the processing circuitry is configured to generate and display one or more sidebars for listing dynamics and emotio-cognition-intensity information based on detected components of the displayed text; the touchscreen, when touched at a position in the display, is configured to select a dynamic or emotio-cognition-intensity; and the processing circuitry is further configured to generate and display color-coded highlighting that designates an occurrence of the selected dynamic or emotio-cognition-intensity.

Further, according to an embodiment of the present disclosure, a further aspect is a system for mitigating a psychological disorder, that can include a mobile device having processing circuitry and memory; and a peripheral device having a communications device and one or more actuators, wherein the memory of the mobile device stores program instructions, which when executed by the processing circuitry of the mobile device, cause the mobile device to perform a method including: receiving, via an input device, the natural language content as a textual input; searching, by the rule-based engine, for matches between a plurality of linguistic rules for a given emotio-cognition and components of the natural language content, wherein instances of the linguistic rules have one or more human dimensions; detecting, by the rule-based engine, the matched linguistic rules to obtain an intensity indication for the given emotion cognition; and when the intensity indication for the given emotio-cognition reaches a negative emotio-cognitional intensity that exceeds a first threshold, transmitting a first activation signal that identifies the negative emotio-cognitional intensity; and the peripheral device is configured to receive, via the communications device, the transmitted first activation signal; and activate the one or more actuators to create a sensory distraction to mitigate the psychological disorder. The foregoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values or dimensions illustrated in the accompanying graphs and figures are for illustration purposes only and may or may not represent actual or preferred values or dimensions. Where applicable, some or all features may not be illustrated to assist in the description of underlying features.

The characteristics and advantages of exemplary embodiments are set out in more detail in the following description, made with reference to the accompanying drawings. In the drawings:

FIG. 6 is a diagram showing types of linguistic rules in accordance with exemplary aspects of the disclosure;

FIG. 17 is a flowchart for operation of an electronic reader in accordance with an exemplary aspect of the disclosure.

FIG. 23 is a flowchart for a method of real time emotion classification in a stream of video/audio in accordance with an exemplary aspect of the disclosure;

DETAILED DESCRIPTION

Figure 1:
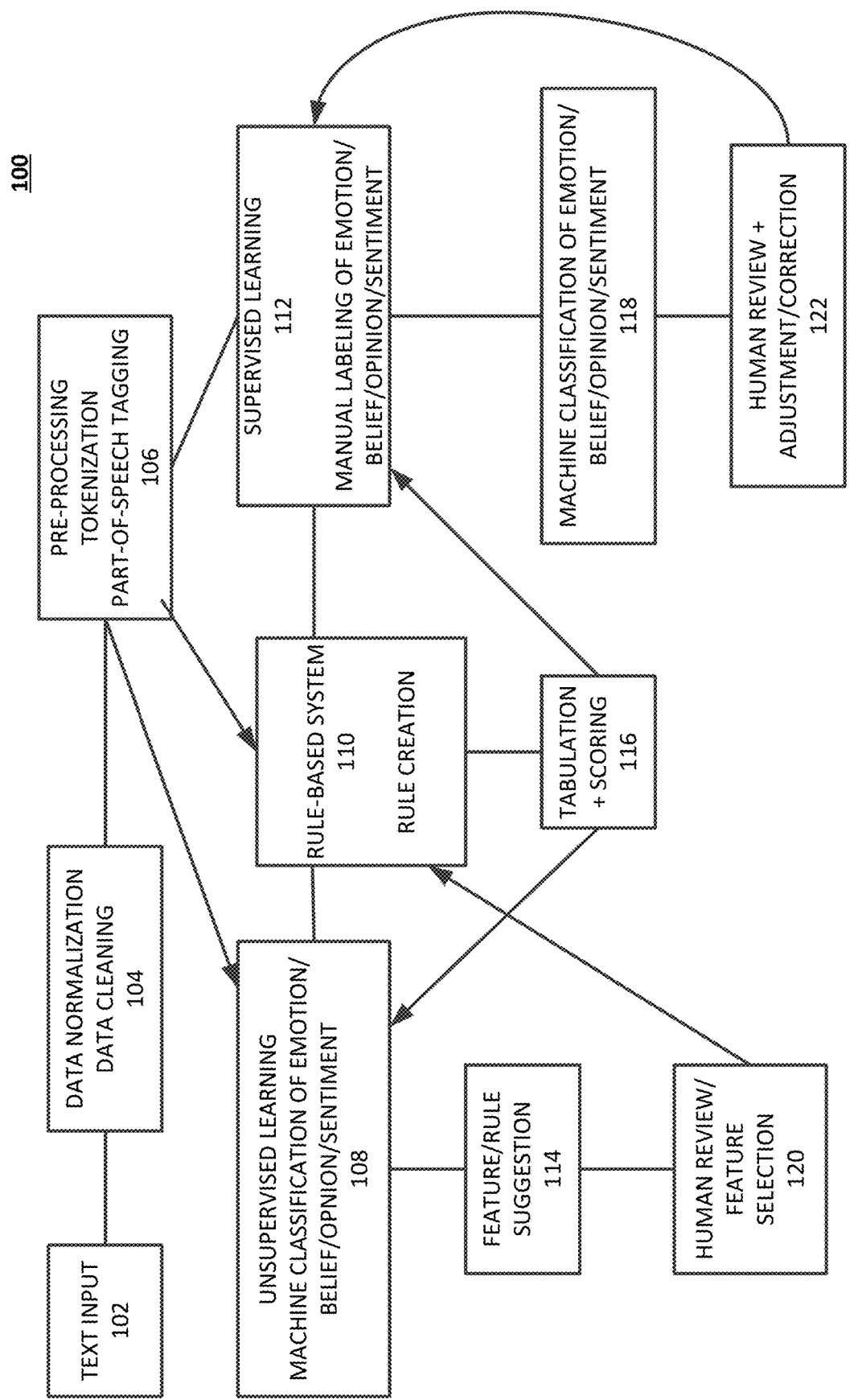
FIG. 1 is a block diagram of a system for automated classification of belief, opinion, sentiment, and emotion in accordance with exemplary aspects of the disclosure.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

As used herein any reference to "one embodiment" or "some embodiments" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. In addition, the articles "a" and "an" as used in this application and the appended claims are to be construed to mean "one or more" or "at least one" unless specified otherwise.

Referring now to the drawings, wherein like reference numerals designate identical or corresponding parts throughout several views, the following description relates to a system and method for automated classification of belief, opinion, sentiment, and emotion. The method optimally includes a linguist rules engine as an input layer to a probability layer, and a layer for determining intensity.

As mentioned above, language is perpetually novel, and even robust tools that can hold so much in memory and effectively look bi-directionally (i.e., BERT) are no match for an evolving natural language. There are countless sentences to be made in the future that cannot be encapsulated by sentences that have come before, including elements like portmanteaus, slang, jargon, metaphor or invented words. Focusing on permutable constructions and mining them for extractable belief, opinion, sentiment, and emotional dimensions allows for more efficient, robust and accurate detection.

Also, in natural language processing, probability is a poor indicator of verbal intensity, because frequency does not necessarily equal intensity. As such, in disclosed embodiments, probability is used as an indication that an emotion is present in a specified portion of a natural language input. Intensity of the emotion is separately determined.

Various techniques may be used for analyzing text in an effort to understand the sentiment, emotion, opinion, or belief that may be expressed or implied by the text. Sentiment may be defined as an attitude, thought, or judgement prompted by feeling. Kin to sentiment is emotion, which may be defined as a strong feeling, such as love, anger, joy, hate, or fear. Emotion may include a conscious mental reaction subjectively experienced as strong feeling and accompanied by physiological and behavioral changes in the body. Opinion may be defined as a belief, judgment, or way of thinking about something. Belief may be something that is accepted, considered to be true, or held as an opinion. For purposes of this disclosure, the term "emotio-cognition" will be used as a term to portray each of sentiment, opinion and belief, emotion, according to its ordinary meaning, judgment, as well as feelings (affect/desires, emotional or sexual bonding), interpersonal/social forces (affinity, community, bonds, influence), cognitive elements (thoughts, opinions, beliefs, stances) and the sentimental space in between (aspirations, values, motivations, regrets).

Disclosed embodiments utilize lexical rules having semantic-syntactic constructions, pre-scored across numerous dimensions, and containing building blocks for semantic sentimental logical operations. Rule-searching measures make tagging easier, faster, and more empirical, and thus reduce the need for GPU-fine-tuning (i.e., fine tuning a pre-trained transformer, such as BERT, GPT2, GPT3), agreement calculations, or high RAM operations. Rule suggestion via dimensional pattern spotting, sentimental occurrence-tracking, and sequence-spotting can also save a tremendous amount of resources tagging, retraining, or using resources to add epochs for accuracy increase or multiple models to solve ambiguity issues. Logical derivation of other sentimental phenomena via aggregation/processing of dimensions allows for simple search-and-count processing per-line instead of heavy calculation, making way for novel calculations (detection of mental health symptoms) without need for a new or specialized training set, new task or added layer.

FIG. 1 is a block diagram of a system for automated classification of emotion in accordance with exemplary aspects of the disclosure. The system 100 includes a text input 102 which receives text from various sources, including a continuous data stream, social media dialog, documents, and whole books. The text received from the text input 102 undergoes a data cleaning and data normalization process 104. Various tools are available for cleaning and text normalization, and generally involve stripping text data of unwanted characters and standardizing words. The choices of which characters are unwanted are user dependent. For example, in some cases punctuation marks may be unwanted. In some embodiments, specific punctuation marks are not removed, but instead may be used in later processing. Specific punctuation marks may include commas, quotation marks, and exclamation marks. Punctuation marks that may be removed may include the at (@) symbol, hashtag (#), dollar ($), percent (%), caret (^), ampersand (&), and asterisk (*). In some embodiments, markups such as HTML tags may be removed. In some embodiments, emoticons may be left intact. In addition, text may be converted to lower case. The cleaned and normalized data is then pre-processed 106, including tokenization, part-of-speech tagging, stemming, and lemmatization. Tokenization splits text into individual elements (e.g., split cleaned text at their whitespaces). Part-of-speech tagging attaches labels to word tokens to identify their part of speech. Stemming is a process of transforming a word into its root form. Lemmatization is a process of obtaining the canonical forms of individual words. Another task may be to remove stop words. The pre-processed data may be formatted for an unsupervised learning process 108, a rule-based system 110, and a supervised learning process 112. A typical method for formatting pre-processed words is to use Google's word2vec algorithm.

The unsupervised learning process 108 may classify the data, including classification of emotion. The unsupervised learning process 108 does not require labeled data, but instead may cluster pre-processed data into classes. The pre-processed data input and resulting classification may be used for feature/rule suggestion 114. Suggested rules and feature selection 120 may be performed to generate future linguistic rules.

The rule-based system 110 may involve creation of predetermined linguistic rules. The predetermined linguistic rules may be organized by categories of emotion.

The supervised learning process 112 requires labeled data. The labeling of emotion may be performed manually. The supervised learning process 112 may be used for machine classification of emotion 118. Errors in classification may be adjusted/corrected 122 in order to improve later classifications. The supervised learning process 112 generates neural models to perform their own classification, which assigns a probability. The neural models also are trained on the rules themselves. They locate similar cooccurrence vectors, similar POS-patterns, and similar n-grams, and suggest these as potential Rules/Suggested Features.

Tabulation and scoring 116 may be applied to the results of the unsupervised learning process 108 and supervised learning process 112. Both the unsupervised learning process 108 and the supervised learning process 112 may output a probability for each class (e.g., using the softmax function).

Figure 2:
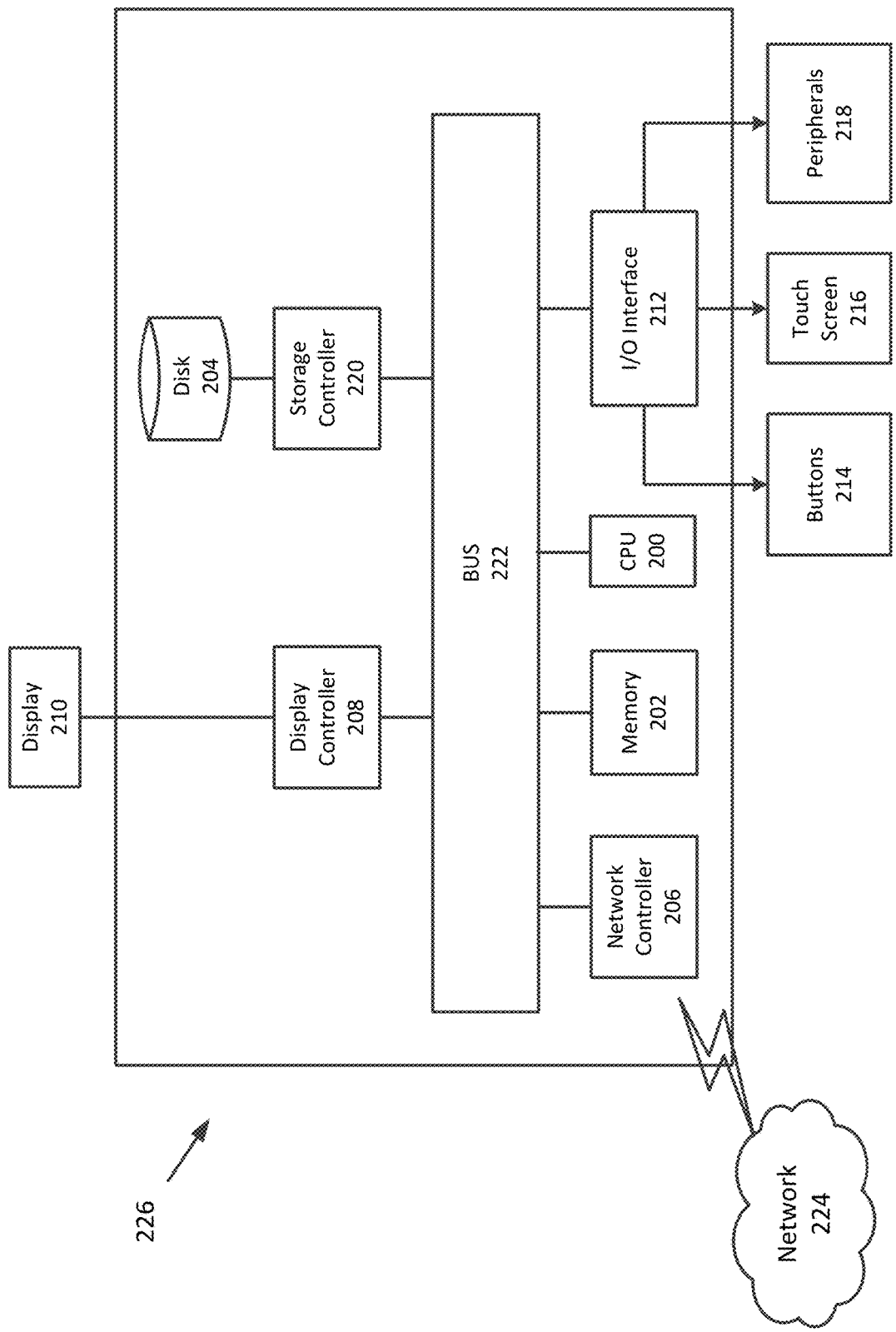
FIG. 2 is a block diagram of a computer system in accordance with an exemplary aspect of the disclosure.

In one implementation, the functions and processes of the system 100 may be implemented by a computer 226. Next, a hardware description of the computer 226 according to exemplary embodiments is described with reference to FIG. 2. In FIG. 2, the computer 226 includes a CPU 200 which performs the processes described herein. The process data and instructions may be stored in memory 202. These processes and instructions may also be stored on a storage medium disk 204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer 226 communicates, such as a server or computer.

Further, the claimed advancements may be provided as a utility application, background daemon, or component of an operating system, or combination thereof, executing in conjunction with CPU 200 and an operating system such as Microsoft® Windows®, UNIX®, Oracle® Solaris, LINUX®, Apple macOS® and other systems known to those skilled in the art.

In order to achieve the computer 226, the hardware elements may be realized by various circuitry elements, known to those skilled in the art. For example, CPU 200 may be a Xenon® or Core® processor from Intel Corporation of America or an Opteron® processor from AMD of America, or may be other processor types that would be recognized by one of ordinary skill in the art. Alternatively, the CPU 200 may be implemented on an FPGA, ASIC, PLD or using discrete logic circuits, as one of ordinary skill in the art would recognize. Further, CPU 200 may be implemented as multiple processors cooperatively working in parallel to perform the instructions of the inventive processes described above.

The computer 226 in FIG. 2 also includes a network controller 206, such as an Intel Ethernet PRO network interface card from Intel Corporation of America, for interfacing with network 224. As can be appreciated, the network 224 can be a public network, such as the Internet, or a private network such as LAN or WAN network, or any combination thereof and can also include PSTN or ISDN sub-networks. The network 224 can also be wired, such as an Ethernet network, or can be wireless such as a cellular network including EDGE, 3G and 4G wireless cellular systems. The wireless network can also be WiFi®, Bluetooth®, or any other wireless form of communication that is known.

The computer 226 further includes a display controller 208, such as a NVIDIA® GeForce® GTX or Quadro® graphics adaptor from NVIDIA Corporation of America for interfacing with display 210, such as a Hewlett Packard® HPL2445w LCD monitor. A general purpose I/O interface 212 interfaces with a keyboard and/or mouse 214 as well as an optional touch screen panel 216, or haptic device on or separate from display 210. General purpose I/O interface also connects to a variety of peripherals 218 including printers and scanners, such as an OfficeJet® or DeskJet® from Hewlett Packard®. The I/O Interface 212 may also connect to a microphone for voice input and speakers and/or headphones for sound output. The microphone and/or headphones may be connected to the I/O Interface 212 by way of an input port, including USB, HDMI, or other peripheral input connection.

The general purpose storage controller 220 connects the storage medium disk 204 with communication bus 222, which may be an ISA, EISA, VESA, PCI, or similar, for interconnecting all of the components of the computer 226.

A description of the general features and functionality of the display 210, keyboard and/or mouse 214, as well as the display controller 208, storage controller 220, network controller 206, and general purpose I/O interface 212 is omitted herein for brevity as these features are known.

Figure 3:
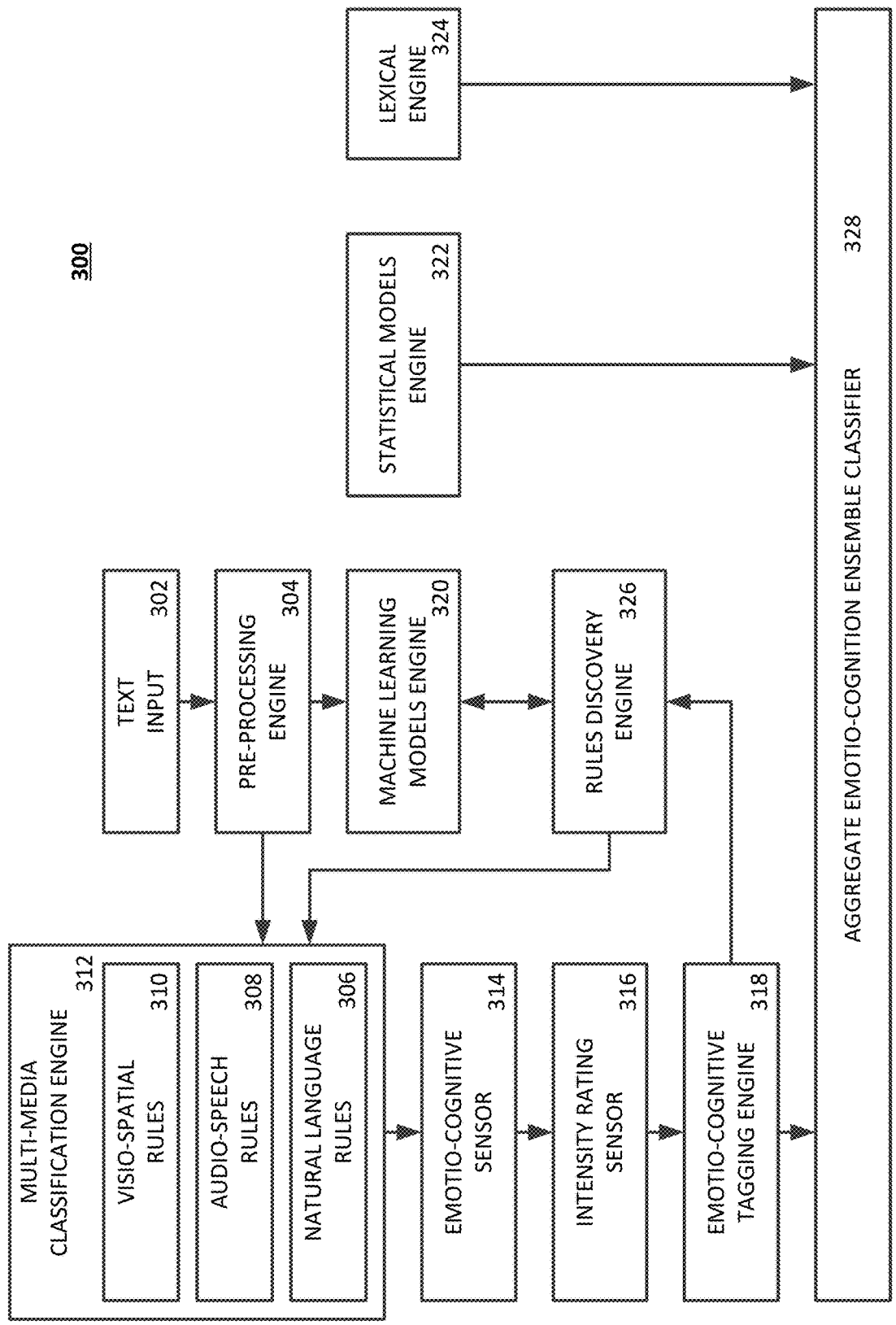
FIG. 3 is a system block diagram for automated classification of emotion in accordance with an exemplary aspect of the disclosure.

FIG. 3 is a system block diagram for automated classification of emotion in accordance with an exemplary aspect of the disclosure. The system 300 includes a multi-media classification engine 312. Multi-media can include video, audio, and text. The multi-media can include scripted or subtitled multimedia, such as audio books, visio-spatial multimedia like movies, TV shows, augmented reality, or virtual reality, which are transcribed and scanned into the system 300. Textual and transcribed media received as input text 302. The input text 302 is processed in the pre-processing engine 304 in order to transform the text data into a form necessary for matching with rules 306, 308, 310, or for input to machine learning models 320. In some embodiments, the pre-processed text data is run through the Natural Language Rules (306). When rules match textual or transcribed media, the rule is said to be fired. Visio-spatial rules 310 can include rules for visual cues. Audio-speech rules 308 can include rules for speech signals.

The Emotio-Cognitive Sensor (314) processes input on a sentence-, paragraph-, passage-, scene-, or chapter-level, and classifies each with a given emotion, cognition, sentiment, state- or dynamic- or trait-based tag. When a rule is triggered, an emotion is detected. Also, linguistic rules have ratings based on Dimensions. In some embodiments, dimension values for a rule are stored as a vector. Emotions can be deduced from the "shape" of the dimensions. Features of emotions include the shape of a vector of the dimensions, the values of the dimensions, and the difference from or similarity to derived calculations from other vectors associated with the rule. The output of the Natural Language Rules 306 is fed to the Emotio-Cognitive Sensor 314 and Intensity Rating Sensor 316, allowing otherwise qualitative data to be transformed into quantitative data for population analysis, as in a scientific study or political poll.

The intensity rating sensor (316) determines intensity ratings for each detected emotion based on the Dimensions. In some embodiments, the Intensity Rating Sensor (316) assigns objective intensity ratings based on subcomponents of each cognitive, emotional, social, interpersonal or state-based element, as the Dimensions.

The Emotio-Cognitive Tagging Engine (318) tags the textual data with the assigned emotion class. Emotion and intensity of emotio-cognition can be associated with metadata, such as demographic information, online profile features, time stamps, sources, geo-locations. A result for aggregate emotio-cognitive states for a sample of the population and labeling of emotio-cognitive states are returned in the Emotio-Cognitive Tagging Engine 318.

A rules discovery engine 326 can generate new rules, also referred to as rules suggestion. The machine learning models 320 can be trained on the rules themselves. The trained machine learning models 320 can locate similar co-occurrence vectors, similar POS-patterns, and similar n-grams, and suggest these as potential new Rules. In addition patterns of emotions as they are detected in the Emotio-Cognitive Sensor (314), as well as dimension patterns may be used to generate new rules.

The machine learning models engine 320 can include any machine learning model or models from among transformer models, such as BERT, RoBERTa, support vector machine, word2vec, KNN model, Long Short-Term Memory model, Convolution Nural Network model.

A statistical models engine 322 can include one or more statistical models. Statistical models can include any statistical model or models from among k-means model, Bayes model, document search models, logistic regression model, linear regression model, polynomial regression model, recommendation matrix, random forest model, and n-gram language model. Each statistical model is used as a classifier.

A lexical engine 324 provides lexicons that can be used in the system 300. Sources of lexicons include NRCLex, Harvard Inquirer, MPQA, sentiwordnet, textblob, VADER, and other lexicons not specifically listed.

In some embodiments, the aggregate emotio-cognition ensemble classifier 328 can output a final answer, such as an emotion. Random Forest can be used as an ensembling classifier, using one-hot coding. In another embodiment, Logistic Regression can be used for ensembling. In a further embodiment, a neural layer can be used as an output of the ensembling. An output can include association of sentiment and intensity of emotio-cognitive sentiment with metadata, such as demographic information, online profile features, time stamps, sources, geo-locations. An output can a pictorial or graphical representation of a user's, brand's, business's, celebrity's, organization's, topic's, word's or phrase's emotio-cognitive summary over a period of or point in time, using a color-based geometrical representation. Optionally, the output can include a report, at any given time or over time, of dimensions, emotions, dynamics, or societal currents for a demographically or otherwise segmented or aggregate sample. Optionally, the output can include generation and display of the distribution of emotio-cognitive state for a given time period, for a single or aggregate users' emotio-cognitive states over time or at a point in time.

Figure 4:
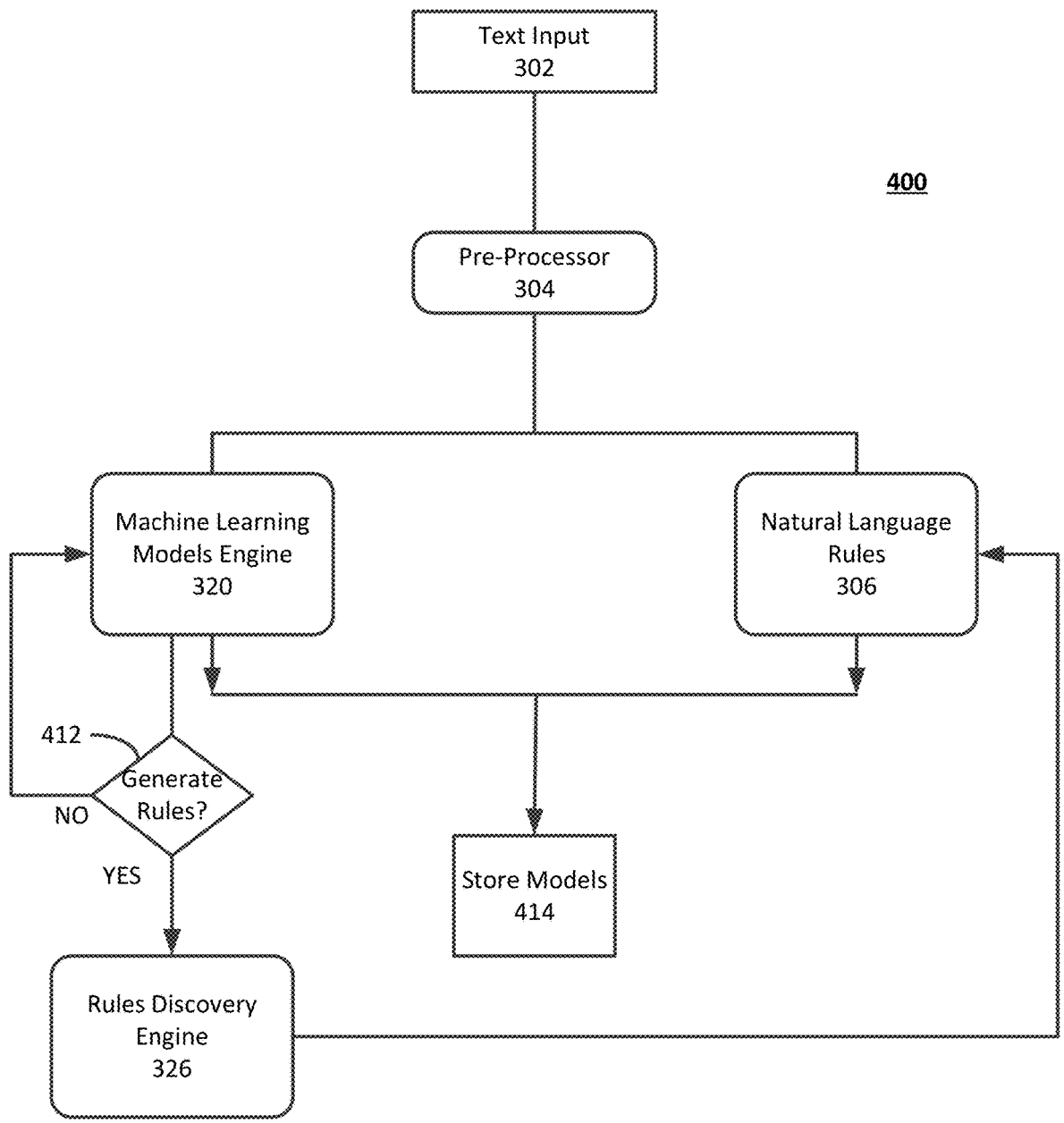
FIG. 4 is a diagram of a training architecture in accordance with an exemplary aspect of the disclosure.

FIG. 4 is a diagram of a training architecture in accordance with an exemplary aspect of the disclosure. In order to accommodate an evolving natural language, the training architecture 400 uses a machine learning models engine 320 to train machine learning models to generate rules. The machine learning models also are trained on the rules themselves. They locate similar co-occurrence vectors, similar POS-patterns, and similar n-grams, and suggest these as potential new Rules.

The linguistic rules model 306 begins with a set of preprogrammed linguistic rules that may be applied to natural language phrases and sentences. Detection can involve potential comparison of these rules, recognition of similarity, and creation of rules that use concatenation of the rule potential elements (rule types). Creation of rules may occur identification of sufficient similarity via a threshold, then creation of tuples of each word with word, part of speech, dependency, stem, and lemma, and matching among similar items based on index position to find the coordinating part of each tuple. The results are then be concatenated, with optional parts, or wildcards, or nearness calculations, as necessary into a concatenated formulaic rule.

The training architecture 400 includes a text input 302 for accessing, via processing circuitry and memory, multiple natural language data items. The multiple natural language data items may be read from a data repository, or may be directly input as a stream of text. The text may include captured, transcribed, or translated text that have originated from human speech input, text databases, documents, or other text data sources.

The training architecture 400 includes a pre-processor 304 for performing various preliminary processes that are typically performed on text for natural language processing. The pre-processor 304 may utilize any of known software libraries for data normalization, tokenization, part-of-speech tagging, stemming, and lemmatization to generate multiple preprocessed natural language data items. An example of software libraries is the Natural Language Toolkit (NLTK). The NLTK includes text processing libraries for classification, tokenization, stemming, tagging, and parsing. The NLTK includes a WordNetLemmatizer having a lemmatize function. Normalization may be performed as canonical normalization.

In some embodiments, the training architecture 300 may involve labeling the multiple preprocessed natural language data items as emotion and an intensity of the expressed emotion. The labels and associated natural language data items may be used to train a supervised learning model.

The training architecture 400 provides the multiple preprocessed natural language data items in parallel to machine learning models engine 320 and a linguistic rules model 306. The training architecture 400 performs training, in parallel, of the machine learning models engine 320 and the linguistic rules model 306 in multiple training epochs to identify, in the natural language data emotion and to determine an intensity of the emotion. Each training epoch of the machine learning models engine 320 may, based on a decision 412, generate feature or rule suggestions 326 for subsequent training epochs of the linguistic rules engine 306. After each training epoch of the linguistic rules engine 306, subsequent epochs of the machine learning models engine 320 are tabulated and scored (provided as probabilities of each class). In 414, an output representing the trained machine learning models engine 320 and the trained linguistic rules 306 is stored in a non-volatile memory.

Figure 5:
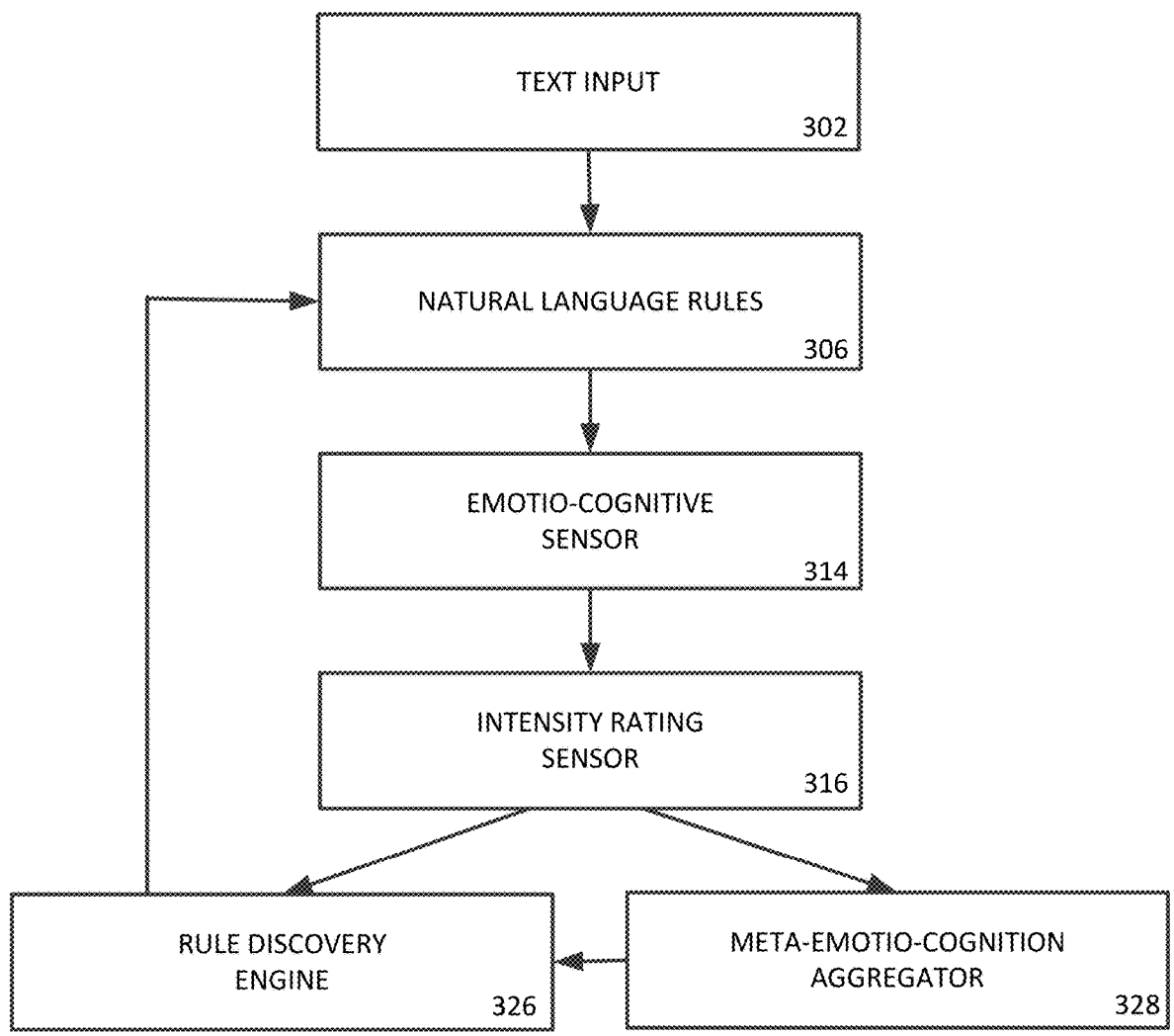
FIG. 5 is a diagram of adaptive operation of the emotion classification system in accordance with an exemplary aspect of the disclosure.

FIG. 5 is a system diagram of adaptive operation of the emotion classification system. The rule discovery engine 326 can generate new rules while presenting emotion and intensity information as an output.

In order to assist in operation, the operation of the emotion classification system will be described in terms of an example. The example is simplified for ease of understanding. The present disclosure is by no means limited to this example. In the example, a hashtagged text "Why am I the one who 'needs' to take out the trash? #NOTANEED" is input 302 by reading the text from a file, or as a continuous stream that is entered into the computer system. The text input is processed by Pre-processing Engine 304, which performs functions including tagging the Input text with an index position, tokenizing the Input text, and separating out the Input hashtag. In some embodiments, the hashtag is a component that has an associated emotion. The index position can be an integer number that indicates a position relative to an overall text, for example a sequential number that is generated by a counter. Alternatively, the index position can be an index such as a vector position, line number, or some input number that identifies where in a sequence of hashtagged text, the current text input occurs. The tokenizing function may selectively separate out punctuation marks, such as "?" as tokens, and may delete others. In the example, the quote marks around "needs" may be preserved in order to indicate an emphasis. The hashtag may be separated out from the other text so that it can be treated as an identifier, rather than as an emotional expression. In some embodiments, the hashtag may be used as an auxiliary indication of the emotion. In this example, the hashtag may indicate that the input text is a sarcasm. Hashtags can also be used to indicate emphasis, commentary/asides, subtweets, organization, continued expression, humor, context, emotions, marketing, protest.

The natural language engine has a function of searching among natural language rules 306 for a rule, or rules, that matches the input text. A rule may indicate a text pattern, with some required words or phrases, mixed with syntax. In the example, a Rule, such as "[why]" [ . . . ]+being verb+"the one who"+verb is pattern matched and triggered.

Rules are grouped by emotions and cognitive terms, and emotio-cognitive blended terms. The Emotio-Cognitive Sensor 314 has a function of applying a Emotio-Cognitive Label (ANGER) based on the triggered rule.

The Intensity Rating Sensor 316 has a function of activating Dimensions for that triggered rule, which can include 3 dimensions with scores—positive, negative, neutral, or null, the dimensions being for example, respect, ego, blame. The values of dimension scores are not limited as such and can include numeric values, in a predetermined range. The Intensity Rating Sensor 316 has a function of aggregating Dimension scores to obtain an intensity score. The Intensity Rating Sensor 316 assigns the intensity score to the Emotio-Cognitive Label and compares the intensity score against a predetermined threshold. The predetermined threshold may be a value, such as 0.6, a percentage, such as 60%, that is common across all emotions, or may be set for each Emotio-Cognitive Label. In this example, according to the threshold, the emotional intensity level is labeled (ANGER—MEDIUM). In some embodiments, the intensity score may also be relative to the speaker, if the speaker's baseline is known.

The Meta-Emotio-Cognitive Aggregator 328 has a function of assessing an Emotio-Cognitive Label and combining the label with other surrounding labels to form a pattern of Emotio-Cognitive Labels, e.g., ANGER_PEACE.

In a next level, a Dynamics 610 has a function of pattern matching the pattern of Emotio-Cognitive Labels with a Dynamic pattern. The Dynamics 610 assigns a label based on the matched Dynamic pattern, e.g., FORGIVENESS.

FIG. 6 is a diagram showing types of linguistic rules in accordance with exemplary aspects of the disclosure. The types of linguistic rules for sentiment, emotion, opinion, and belief, that are applied to the specified portion of the natural language input can include a rule that uses part of speech tagging or syntax (502), including granular types of Parts of Speech: e.g., modal verb and optative, tense notations, declension, conjugation, accents, as well as direct objects, and proper nouns.

a rule that uses string matching, including exact, inexact, masked or wildcarded (504), a rule that uses distance between tokens (506), a rule that uses punctuation (508), a rule that uses lemmatization (510), a rule that uses stemming (512), a rule that uses lexicon (514), and a rule that uses word lookup or dictionary (516).

In some embodiments, rule components may include graphical content, including Emojis, Glyphs, Emoticons, and any other graphemes. Applying the linguistic rules to the specified portion of the natural language input results in obtaining the numeric or Boolean value for each of the one or more linguistic rules.

The linguistic rules are grouped by types of emotion or cognition. In some embodiments, rules may have an order of importance, and the order may be changed, to indicate precedence over rules below it, and under rules above it. Each linguistic rule has one or more dimensions and a value for each dimension. In one embodiment, dimensions may include of Emotio-Cognitive attitudes, values, social mores, mindsets, outlooks, aspects, responses, traits, beliefs, opinions, perspectives, motivations, biases, states, manners, approaches, and dynamics. In one embodiment, dimensions can include emotional affects of: positive, negative, anger, anticipation, disgust, fear, joy, sadness, surprise, and trust (from NRCLex), as well as objective, subjective, neutral, polarity. In another embodiment, dimensions can include, but not limited to, emotional affects of: ego, blame, conformity, sacredness, kindness, respect, time (future), (self) favor, approval, sincerity, vulnerability, judgment, separateness, purpose, formality, minimization, specificity, force, action (activeness), agency, curiosity, clarity, intention, emphasis, energy, certainty, interest, engagement, shock/surprise, tension, speed, nuance, logic, paranoia, trust, distance, identification w/, esteem (self), esteem (other), objectification, attachment, empathy, and patience. In some embodiments, dimensions may include categories, such as personality trait, belief, opinion, perspective, aspect, motivation, bias, state, emotional approach/choice, manner, reaction, interpersonal dynamic.

The inventors have found that even entirely accurate classification can still yield very limited semantic information. Sentences, phrases, or constructions remain poorly classified for specific affect and deep semantic value, parsed on the sentence-level, oftentimes forced into a single class where multiple labels should apply, or unable to be accurately understood by machine algorithms, due to the complexity and depth of human emotion. Additionally, while conversation can be mined for further information, discursive text value has been limited to contextual clues approaches such as Named Entity Recognition and speaker-specific information, yielding little about affective states.

Despite the existence of state-of-the-art technology such as transformers, these have only historically excelled at prediction and translation tasks, rather than semantic interpretation (in part, due to poorer performance on semantic tasks). Transformers are ultimately limited in their semantic capacity, due to the gap between human and machine interpretative ability. Among the semantic limitations, particularly with interpreting extemporaneous speech and text, are the ability to identify mixed emotions, complex emotions, figurative expression and insincere emotional expressions (such as sarcasm, irony, politeness, and passive aggression). Disclosed embodiments are an approach to handling range and depth of human emotion and cognition.

Figure 7:
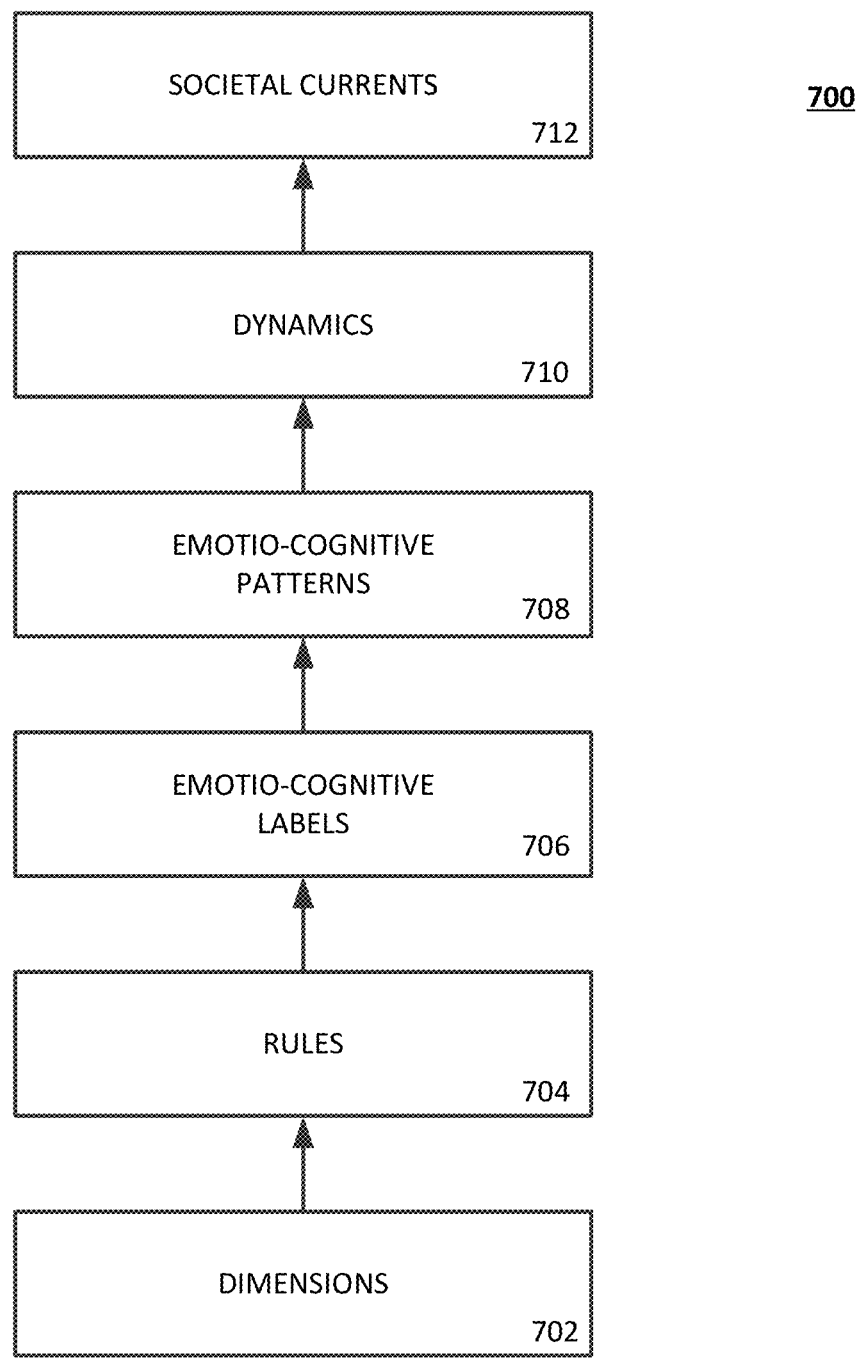
FIG. 7 is a bottom-up stack for layers of the rules engine in accordance with exemplary aspects of the disclosure.

FIG. 7 is a bottom-up stack for layers of the rules engine. "Dimensions" (702) are elements of emotions. In some embodiments, the system is implemented using object-oriented programming and emotions are a class having a set of dimensions as attributes of the class. Intensity is a method of the emotion class and is determined based on the presence of dimensions. The emotion class has prototypical values for each of the attributes/dimensions. The values of dimensions are tiny valences with trinary values (+1 positive force, −1 negative force, 0 neutral force, and Ø not present/not applicable; the latter 2 of which are not equivalent). In some embodiments, the values for dimensions include layers of Boolean, such as (1) TRUE-FALSE (Neutral vs. Not), (2) TRUE-FALSE (True vs. False), (3) Potentially similarly with null. The values may be n the form of floating point numbers or integers.

These dimensions receive ratings every time a rule is triggered. So, for instance, for the example ("[why/how come]+BEING-V+PRON+[TIME-HYPERBOLE]+"the one/s who"+VERB"), which denotes a construction with: an optional Word List item (of 2 items: "why" or "how come")+a being verb plus a pronoun ("are you"/"am I"/"are they"/"are we"/"is he"/"is she," etc.)+an optional Word List item for Time Hyperbole ("always", "never", "constantly", etc.)+exact string with a wildcard after the e in "one" ("the ones who", "the one who")+ virtually any verb ("sits up front", "pays for everything", "brings up problems", "gets the easy job", etc.) The rule uses those parts that are modular, and covers some degree of permutation.

The rules detect a given emotion's dimensional profile. Different rules find different and partial but strongly matching configurations, which represent emotional states. In other words, emotions are mental states. Primal emotions are pure and unreasoning (e.g., fear, anger, happiness, sadness). Complex emotions are more social and cognitive (e.g., grief, depression, shame, insecurity, admiration). Complex emotions occur when cognitive states and emotional states co-occur, or when multiple emotions are co-occurring. When rules are activated, they provide an indication of when such emotional states are occurring.

The more dimensions that match a particular emotion, the higher the intensity of that emotion. Subsequently, the measure of intensity is an objective measure and represents a degree of intensity. In some embodiments, if the same construction happens twice in an input text, the matching construction is counted both times. In measuring intensity, Dimension scores are normalized over the number of words. Thus intensity values are density-based.

In an example embodiment, there are 50 dimensions. In some embodiments, there are a greater number of dimensions, for example about 20% more dimensions. Each rule has ratings across the entire set of dimensions.

Each rule 704 includes one or more Dimensions. For the above rule, one example dimension is Ego. Ego can be absent from a given construction (have nothing to do with it null value), be neutral (there's an ego component, but it's very even and fair), be positive (egotistical, condescending), or negative (admiring, supplicant, self-blaming, etc.). Ego is a dimension that is rated for this rule. Another dimension is curiosity. This construction detected by this rule is proactively curious, so it receives a +1 rating.

Rules 704, once activated, indicate detected Emotions. Once the Emotions have been detected (in the portion of the sentence they exist; tagging is performed via index position instead of simply sentence- or passage-level, which allows for greater distinction and clarity), complex emotions 706 can be identified, and these usually are comprised of simultaneous emotions. For instance, contempt is a combination of pride/condescension and anger. In addition, emotio-cognitive states can overlap.

Once complex and primal Emotions have been activated in place, patterns of emotions 708 can be assessed, as emotions naturally shift to other emotions, in particular situations. In addition, emotions can progress, escalate, or resolve. Patterns of emotions 708 are formed by concatenating emotions into an ordered array, or a string, of emotions (e.g., HOPE+EXPECTATION+SURPRISE+SADNESS). These patterns can be assessed somewhat like a skip-gram model with limited possibilities. Patterns for shifting emotions, progressing emotions, escalating emotions, and resolving emotions are stored as recognizable emotional patterns.

The patterns of emotions can be used to predict flows of Emotion: excitement turning to acceptance to calm; anger shifting to confusion, realization, and back to love as understanding arises and empathy or forgiveness develop, etc.

The Emotional Patterns build to Dynamics 710. Dynamics 710 are descriptive labels for major emotional events that summarize patterns of emotion. For example, a Dynamic of "DISAPPOINTMENT" is a label for an emotional pattern of HOPE+EXPECTATION+SURPRISE+SADNESS.

Dynamic can happen within the Self—this is usually the complex emotion. Next, the Dynamic can happen with the Other/interpersonally—this might be a phenomenon like Forgiveness. In such case, FORGIVENESS is a label for an emotional pattern of ANGER+REALIZATION+LOVE.

A layer above Dynamics 710 may include a Societal currents 712, which are meta-results of strong emotional dynamics en masse, often brought to a head by the pressure of major events or mass movements—such as unrest or innovation. Major events can include impending real-world events (anger explosion, coup, trend, gamestop stock buyup, domestic violence breaking point, falling in love, resentment, canceled). Detection of Societal Currents enables reaction/prevention or capitalization, or at least passively monitoring/identification. Such events can be correlated with specific, past such real-world events with these Societal Currents, enabling speedy reaction, prevention or capitalization upon if similar events are able to be quickly detected or predicted in the future. Computation of emotio-cognitive states, Dimensions, Dynamics, and Societal Currents, from natural language from one or more user, via the Natural Language Rules 306.

In some embodiments, each level of Emotional/Cognitive flow can be predicted for these layers based on historical data, stored as the classification system is being used.

Figure 8:
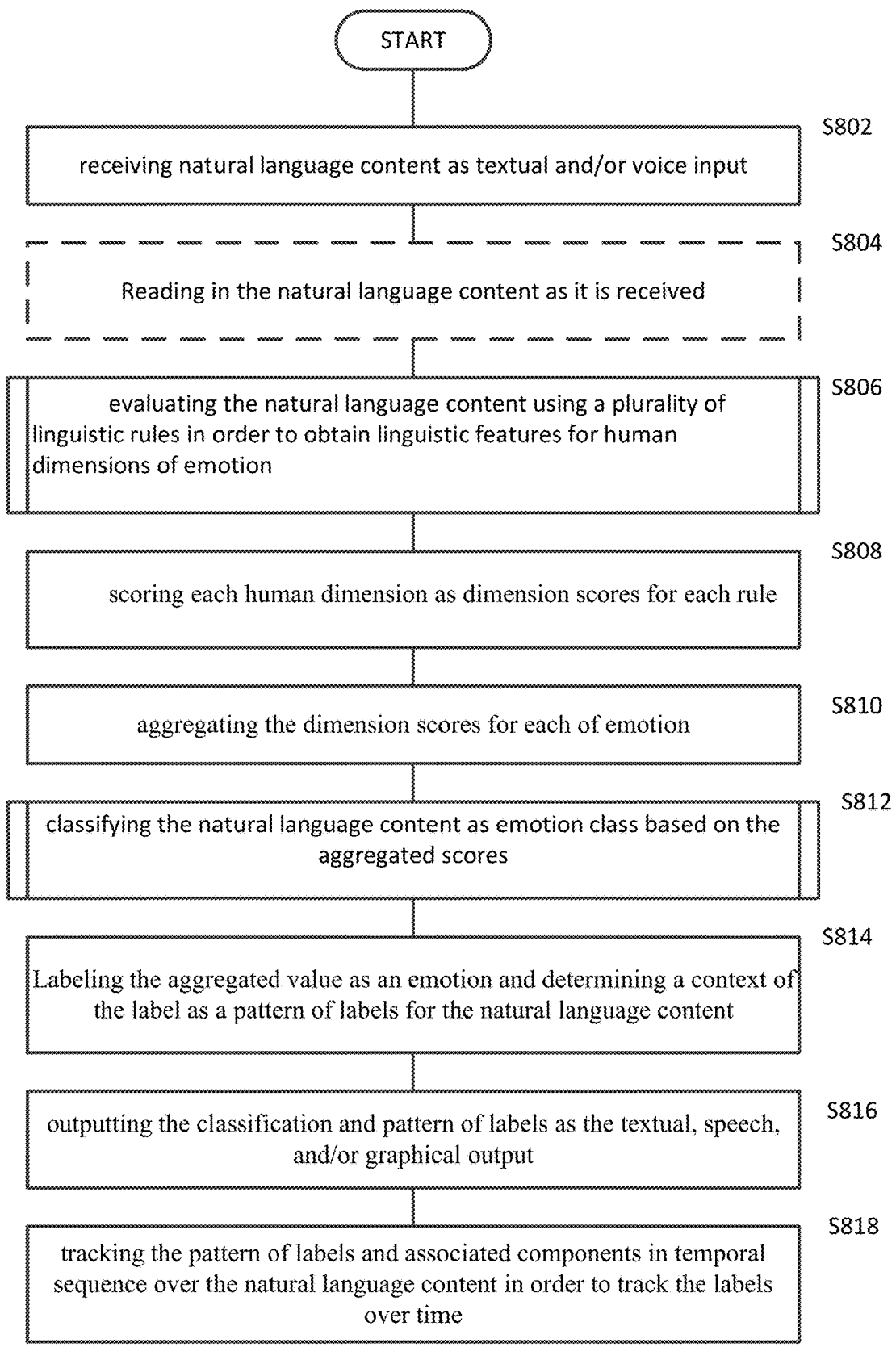
FIG. 8 is a flowchart of a method of operation of a computer system in accordance with an exemplary aspect of the disclosure.

FIG. 8 is a flowchart of a method of operation of a computer system in accordance with an exemplary aspect of the disclosure. One embodiment relates to a process of tracking nuanced psychological affect in natural language content. The method first applies linguistic rules for emotion to natural language constructions, phrases, or sentences, each rule having one or more dimensions. The results of applying the linguistic rules are used to detect emotion and determine intensity of emotion. A machine learning model is used to suggest new linguistic rules, and thus serves to augment the application of the linguistic rules. The process may be performed in a device having a textual and/or voice input and a textual, speech, and/or graphical output. A computer program includes instructions stored on a computer-readable storage medium, which when executed by a computer system, as in FIG. 2, performs steps as shown in the flowchart.

In S802, the computer 226 is configured to receive the natural language content as text, which may be derived from the textual and/or voice input. The natural language content may be read from a file stored in the disk storage 204, or may be read from a stream of data received at network controller 206, or from text input at a keyboard 214, or from text from voice input via a microphone. In addition, input can include aggregation of data, from an online or offline database, query, taken from a historical archive or corpus, or scraped from a website, such as a social media or user review website. Input can include unprompted or prompted, concerning a topic, person, brand, organization, concept, word, or group of words. Input can include interview data, transcribed or otherwise obtained from participants in surveys, market research, or academic studies. In some embodiments, the input may include time stamps, which may be read in conjunction with the natural language content.

For large sections of text that may exceed the size for an input text that is handled by the natural language rules engine 306 or machine learning models engine 320, one approach is to read the input using a sliding window of fixed size. In optional step S804, the computer 226 is configured to apply a scanning window of fixed length to the natural language content. The length may be a number of characters. The scanning window may overlap by a certain number of characters between successive movements of the scanning window. In step S806, the computer 226 is configured to evaluate the natural language content using the linguistic rules for each emotion in order to obtain linguistic features for human dimensions of emotion. As described above, linguistic rules are patterned matched with the natural language content.

In S808, the computer 226 is configured to score each human dimension for presence, neutrality, level or absence as dimension scores for each matched rule.

In S810, the computer 226 is configured to aggregate the dimension scores for each emotion to obtain an intensity score for the respective emotion. The aggregated scores represent intensity of an emotion. In some embodiments, the starting index and ending index in the natural language content for the emotion is determined for each particular dimension. In some embodiments, the indexed natural language content and corresponding dimension may be forwarded to the machine learning models engine 320. In some embodiments, the top dimension for emotion may be forwarded to the machine learning models engine 320 together with a respective numerical (dimension score) or mapped descriptor. Patterns of emotion including the starting index and ending index may be stored for an entire passage having several constructions, phrases and sentences.

In S812, the computer 226 is configured to classify the natural language content as an emotion class based on the dimension scores. In some embodiments, the classifying may generate a probability for each emotion class.

In S814, the computer 226 is configured to label the aggregated value as an emotion and determine a context of the label, such as a pattern of emotion labels, for the natural language content.

In S816, the computer 226 is configured to output the classification and pattern of emotion labels as the textual, speech, and/or graphical output.

In S818, the computer 226 is configured to track the pattern of emotion labels and associated components in temporal sequence over the natural language content in order to track the emotion labels over time. Each emotion label can be assigned an ordered index number to identify their order in sequence. In the case of natural language content that includes time stamps, each emotion label may be assigned a time stamp of the associated components.

Figure 9:
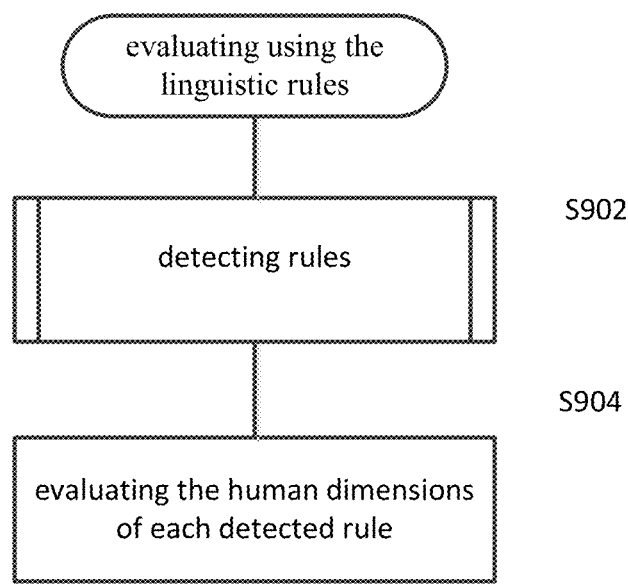
FIG. 9 is a flowchart for steps for evaluating using linguistic rules in accordance with an exemplary aspect of the disclosure.

FIG. 9 is a flowchart for steps for evaluating using linguistic rules in accordance with an exemplary aspect of the disclosure. The evaluating using the plurality of linguistic rules of S806, includes the following steps.

In S902, the computer 226 is configured to detect rules using rule pattern matching; and In S904, the computer 226 is configured to evaluate the human dimensions of each detected rule.

Figure 10:
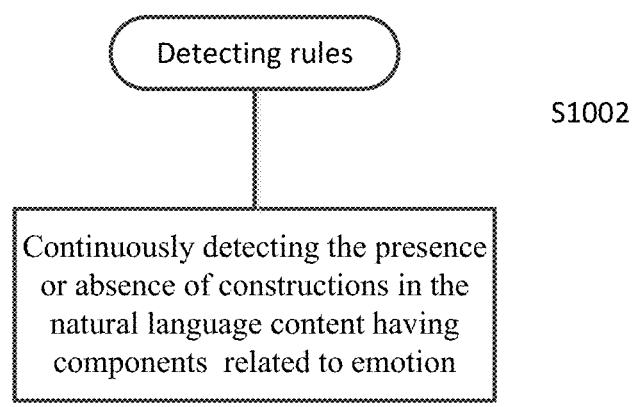
FIG. 10 is a flowchart for detecting rules in accordance with an exemplary aspect of the disclosure.

FIG. 10 is a flowchart for detecting rules in accordance with an exemplary aspect of the disclosure. The detecting of rules of S902, includes S1002, detecting presence or absence of constructions in the natural language content having components related to an emotion.

Figure 11:
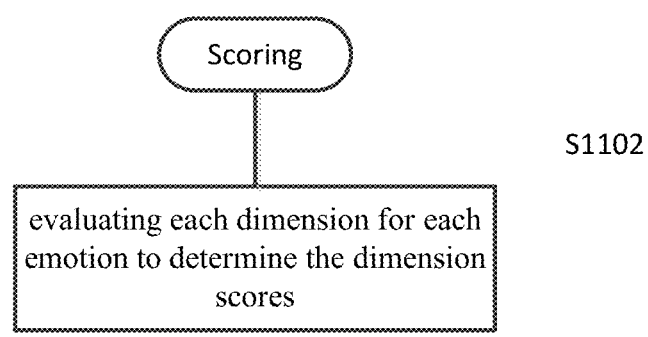
FIG. 11 is a flowchart for scoring in accordance with an exemplary aspect of the disclosure.

FIG. 11 is a flowchart for scoring in accordance with an exemplary aspect of the disclosure. The scoring of S808, includes S1102, evaluating each dimension to determine the dimension scores.

Figure 12:
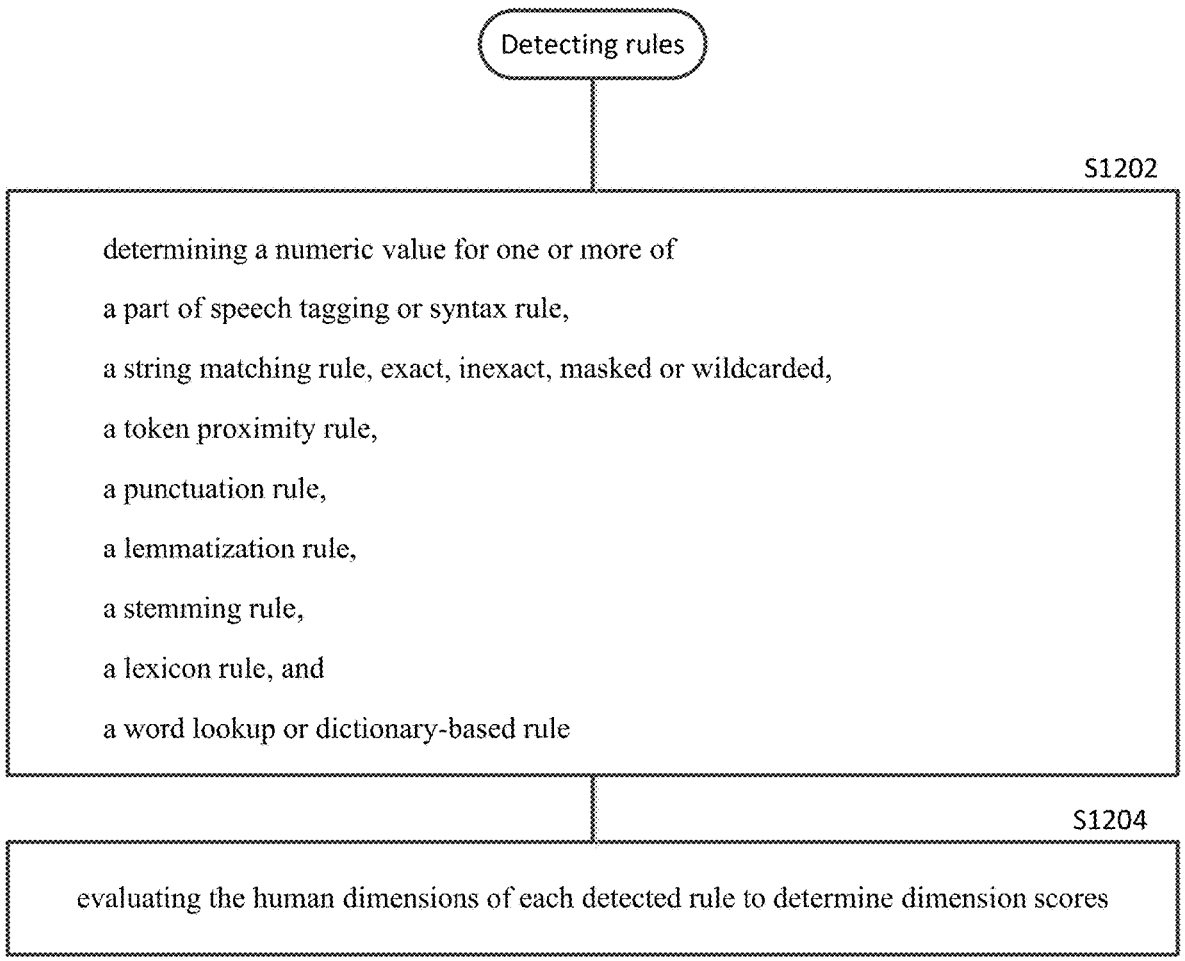
FIG. 12 is a flowchart for detecting rules in accordance with an exemplary aspect of the disclosure.

FIG. 12 is a flowchart for detecting rules in accordance with an exemplary aspect of the disclosure. The detecting rules, among the plurality of linguistic rules, of S702, includes S1202, determining numeric values for
  a part of speech tagging or syntax rule,
  a string matching rule, exact, inexact, masked or wildcarded,
  a token proximity rule,
  a punctuation rule,
  a lemmatization rule,
  a stemming rule,
  a lexicon rule, and
  a word lookup or dictionary-based rule.

Figure 13:
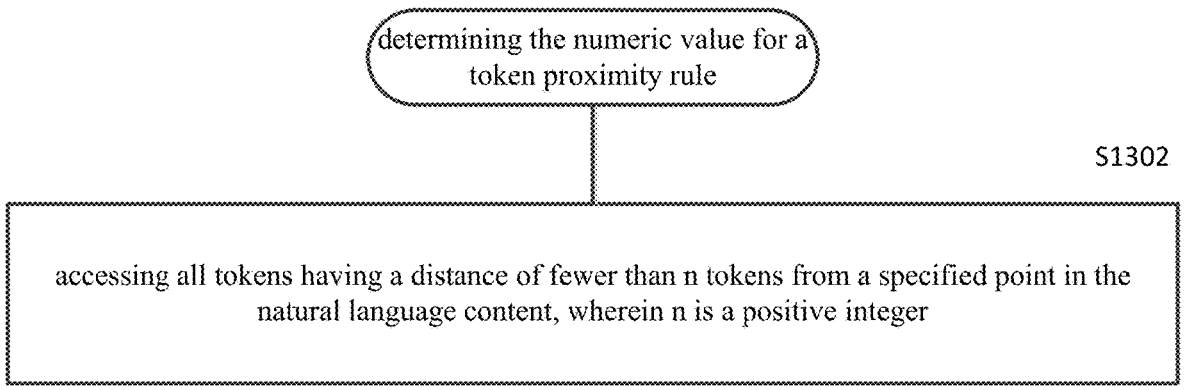
FIG. 13 is a flowchart for determining numeric value for a token proximity rule in accordance with an exemplary aspect of the disclosure.

FIG. 13 is a flowchart for determining numeric value for a token proximity rule in accordance with an exemplary aspect of the disclosure. The determining the numeric value for a token proximity rule includes accessing all tokens having a distance of fewer than n tokens from a specified point in the natural language content, wherein n is an integer.

Figure 14:
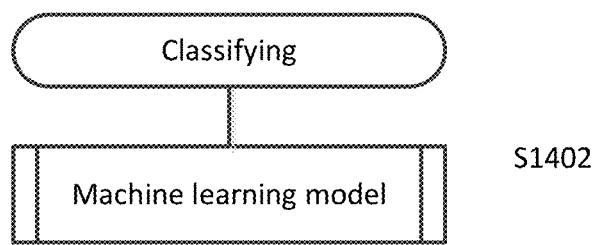
FIG. 14 is a flowchart for classifying in accordance with an exemplary aspect of the disclosure.

FIG. 14 is a flowchart for classifying in accordance with an exemplary aspect of the disclosure. The computer 225 is configured to perform the classifying of S812 using a machine learning method, including any of supervised learning, unsupervised learning, and a rule-based system.

Figure 15:
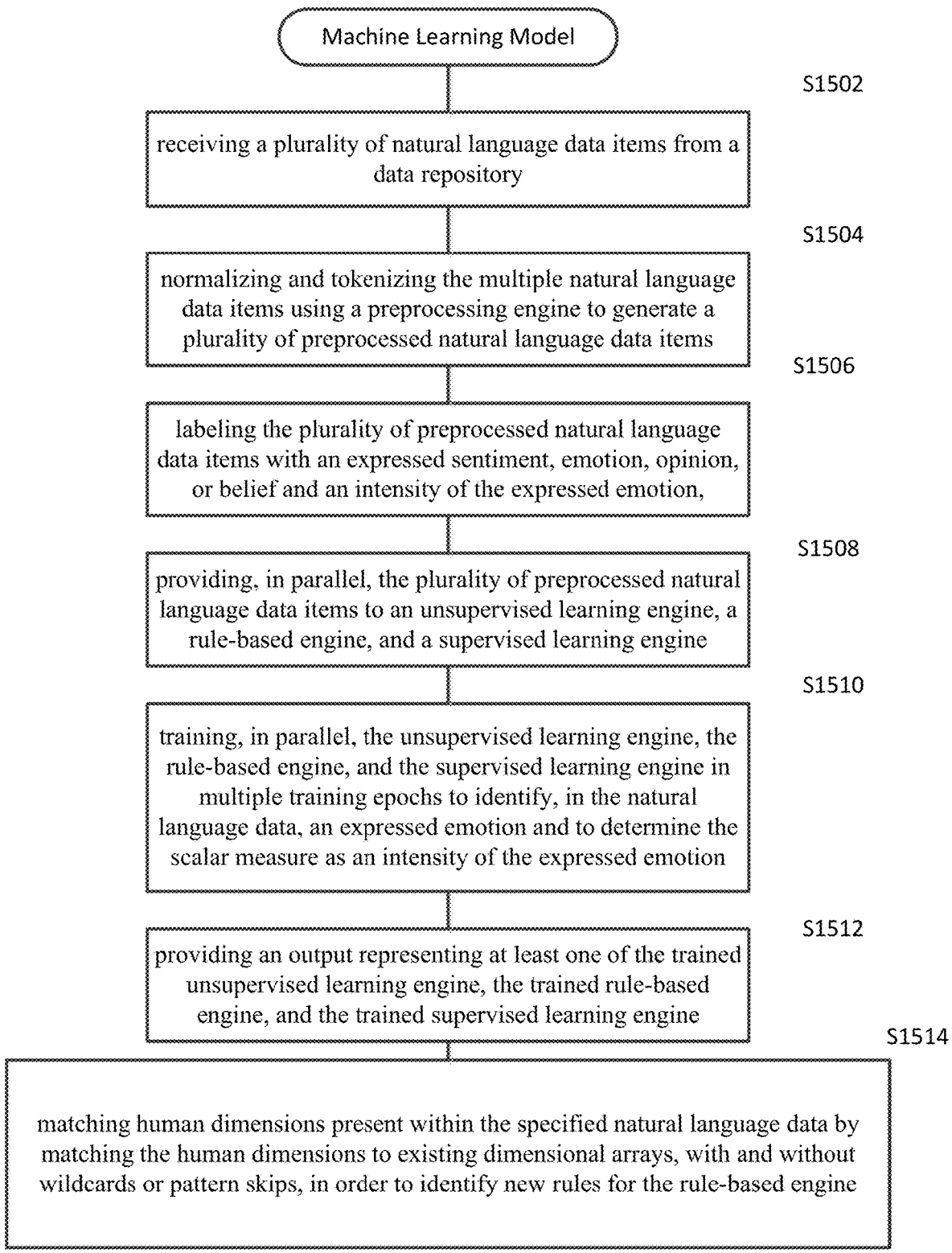
FIG. 15 is a flowchart for hybrid multi-model learning in accordance with an exemplary aspect of the disclosure.

FIG. 15 is a flowchart for machine learning in accordance with an exemplary aspect of the disclosure. The machine learning of S1402, including S1502, receiving a plurality of natural language data items from a data repository;

S1504, normalizing and tokenizing the plurality of natural language data items using a preprocessing engine to generate a plurality of preprocessed natural language data items, which may include pre-sorting data lines into Positive, Negative and Neutral, in order to save computing power and time in classification;

S1506, labeling the plurality of preprocessed natural language data items with an expressed sentiment, emotion, opinion, or belief and an intensity of the expressed sentiment, emotion, opinion, or belief;

S1508, providing, in parallel, the plurality of preprocessed natural language data items to an unsupervised learning engine, a rule-based engine, and a supervised learning engine;

S1510, training, in parallel, the unsupervised learning engine, the rule-based engine, and the supervised learning engine in multiple training epochs to identify, in the natural language data, an expressed emotion, and to determine the scalar measure as an intensity of the emotion.

Each training epoch of the unsupervised learning engine provides feature or rule suggestions to subsequent training epochs of the rule-based engine, and each training epoch of the rule-based engine provides tabulation and scoring data to subsequent epochs of the unsupervised learning engine and the supervised learning engine.

In S1512, an output is generated representing the trained unsupervised learning engine, the trained rule-based engine, and the trained supervised learning engine.

In S1514, human dimensions present within the natural language data are matched by matching the human dimensions to existing dimensional arrays, with and without wildcards or pattern skips, in order to suggest new rules for the rule-based engine.

The system allows for deduction or recognition of the points and levels (intensities) at which feeling turns to action (as described within, and detected by, the text). The system allows for the recognition of dynamics within the self, on a bipersonal (one-on-one), interpersonal/multi-personal or family, or society (community, country, region, or world). The system allows the tracking of intensity of emotion as it fluctuates throughout the sentence, item/paragraph and passage. The system allows for the identification of large, important shifts in perception, such as a sharp turn in aggregate self-image (via ego dimension), which may indicate a problem or significant change has arisen. The system can reveal the relationship between important factors, via correlation, such as the relationship between self-esteem/self-image and general optimism.

Numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims.

EXAMPLE IMPLEMENTATIONS

Electronic Reading Device

Embodiments of the present invention include an electronic reader. An electronic reader can be a dedicated device that incorporates specialized firmware and a display that is configured to optimally display text with high clarity (commonly referred to as an Ebook Reader), or can be a general purpose computing device, such as a tablet computer or smartphone, that is configured with software for text reading, typically in the form of a mobile application (App). An electronic reader has a display screen that is generally 10 inches diagonal or less, and has limited computer processing capability and memory. In most cases, the electronic reader can communicate with a web service via an Internet connection, typically by way of a WiFi connection. Some electronic readers include a communications module for communication by way of cellular transmission.

The system 300 having a multi-media classification engine 312 can be performed in a device with limited processing power and memory, as most of the processing is based on execution of the natural language rules engine 306. The machine learning models engine 320 may be performed off-line in a separate computer, or in a cloud service.

Figure 16:
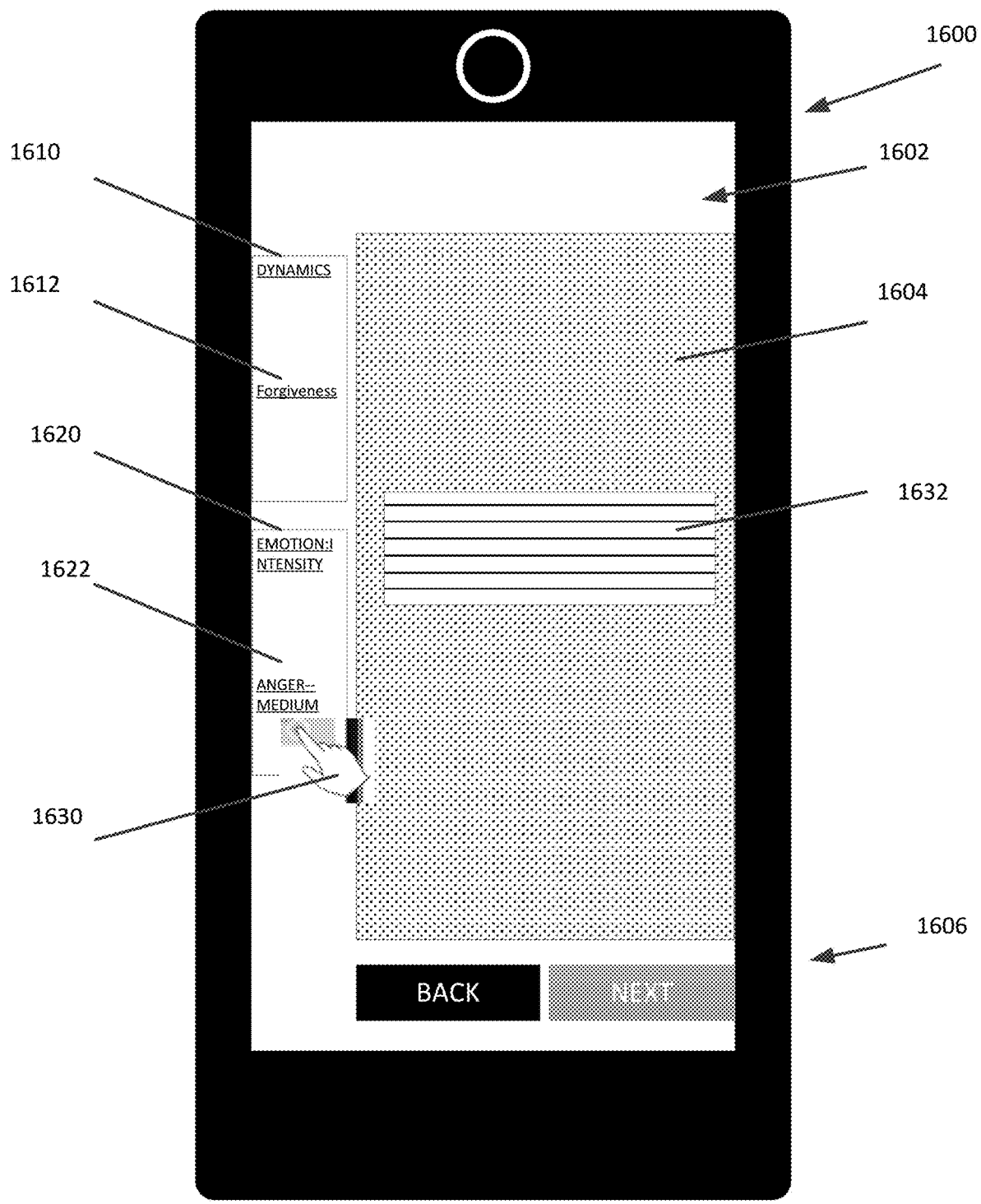
FIG. 16 illustrates an electronic reader in accordance with an exemplary aspect of the disclosure.

FIG. 16 illustrates an electronic reader in accordance with an exemplary aspect of the disclosure. An electronic reader 1600 includes a display screen, or touchscreen display 1602. When the display 1602 is displaying text of a book 1604, the display may include scrolling functions displayed as scrollbars (not shown), and page turning functions, displayed as buttons 1606.

FIG. 17 is a flowchart for operation of an electronic reader in accordance with an exemplary aspect of the disclosure. In S1702, the system 300 may assess a written fiction or nonfiction work for emotional, cognitive, interpersonal or social dynamic, motivation, belief, opinion, or psychological elements, by multi-media classification engine 312. In S1704, text in an electronic book is scanned and tagged with rules that trigger, emotional, cognitive or otherwise states that are identified, and the intensity with which they have occurred.

In an embodiment, in S1706, the system 300 may generate and display color-coded highlighting that designates occurrence of certain emotional or cognitive or sociological or interpersonal dynamics and/or states. In an embodiment, in S1708, the system 300 may generate and display one or more sidebars for dynamics 1610 and emotion-intensity 1620. The sidebars may summarize the emotional, psychological, cognitive, sociological, or interpersonal dynamics or states that occur within the text 1604, with added context where available. In S1710, each dynamic 1612 or state 1622 can be interacted with by selecting 1630 (via touch, mouse, keyboard, etc.) allowing the electronic reader 1600 to be presented with examples 1632 within the text of that given dynamic or state.

Multimedia Audio Book or Visio-Spatial Data Sentiment Classifier

The system 300 having a multi-media classification engine 312 can be performed in a device with limited processing power and memory, as most of the processing is based on execution of the natural language rules engine 306. The system 300 performs emotion classification for sentences, phrases, and constructions, and can perform the emotion classification in real time as text is being received. The machine learning models engine 320 may be performed off-line in a separate computer, or in a cloud service.

Figure 18:
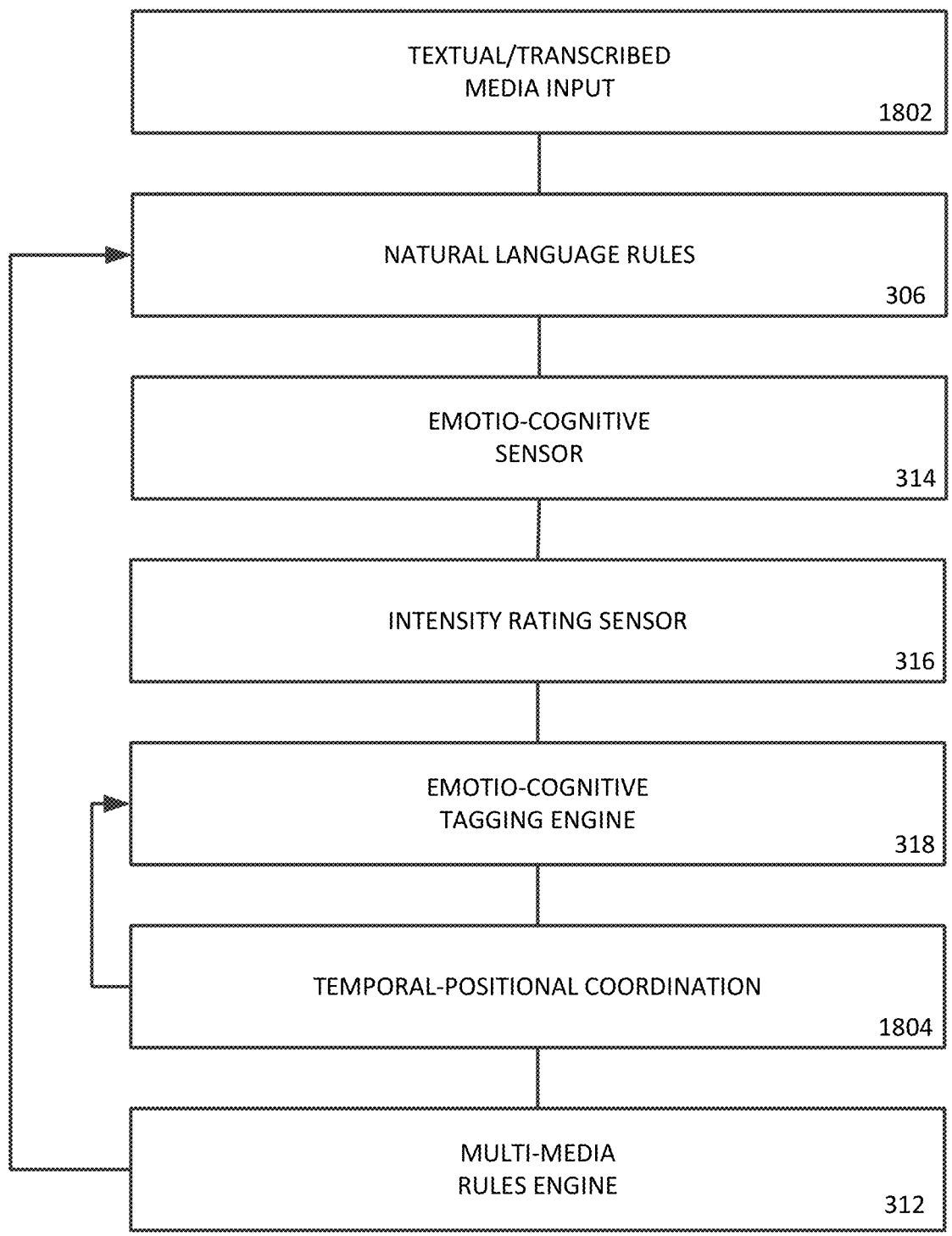
FIG. 18 is a flow diagram of the system for a Multimedia Audio Book or Visio-Spatial Data Sentiment Classifier in accordance with an exemplary aspect of the disclosure.

FIG. 18 is a flow diagram for a Multimedia Audio Book or Visio-Spatial Data Sentiment Classifier in accordance with an exemplary aspect of the disclosure.

Scripted or subtitled multimedia, such as audio books, or visio-spatial multimedia like movies or TV shows, can be scanned into the system and transcribed into text.

In 1802, textual and transcribed media is run through a Natural Language Rules Engine (306), matching to rules.

The Emotio-Cognitive Sensor (314) processes input on a sentence-, paragraph-, passage-, scene-, or chapter-level, and classifies each with a given emotion, cognition, sentiment, state- or dynamic- or societal-based tag. Stray, short or partial strings and select individual words, known as High Use Non-Construction Hooks (HUNCHes) with partial dimensions are detected within the text and matched.

The Intensity Rating Sensor (316), analyzes text and assigns objective intensity ratings based on subcomponents of each cognitive, emotional, social, interpersonal or state-based element, known as Dimensions.

The Emotio-Cognitive Tagging Engine (318) tags the textual data with the assigned class.

The Temporal-Positional Coordination (1804) makes timing-based associations between the textual information's tagged classes and the coordinated sections of auditory or visual data and signals, which are then classified and sent to the Emotio-Cognitive Tagging Engine (318) to be tagged.

The systems 300 scans for further instances of matching audio or visual patterns, both absolute and relative to the Speaker's audio or visual baseline, and adjusted for gender, age, class, race, accent, locale and other demographic information, and situational information, automatically tagging them with Emotio-Cognitive classes associated with the pattern in question.

Text coordinated with auto-tagged emotional classes in the prior step become automatically flagged in the text as matches to, or flagged as high-likelihood for, the Emotio-Cognitive classes now borne by the audio or visual data.

Figure 19:
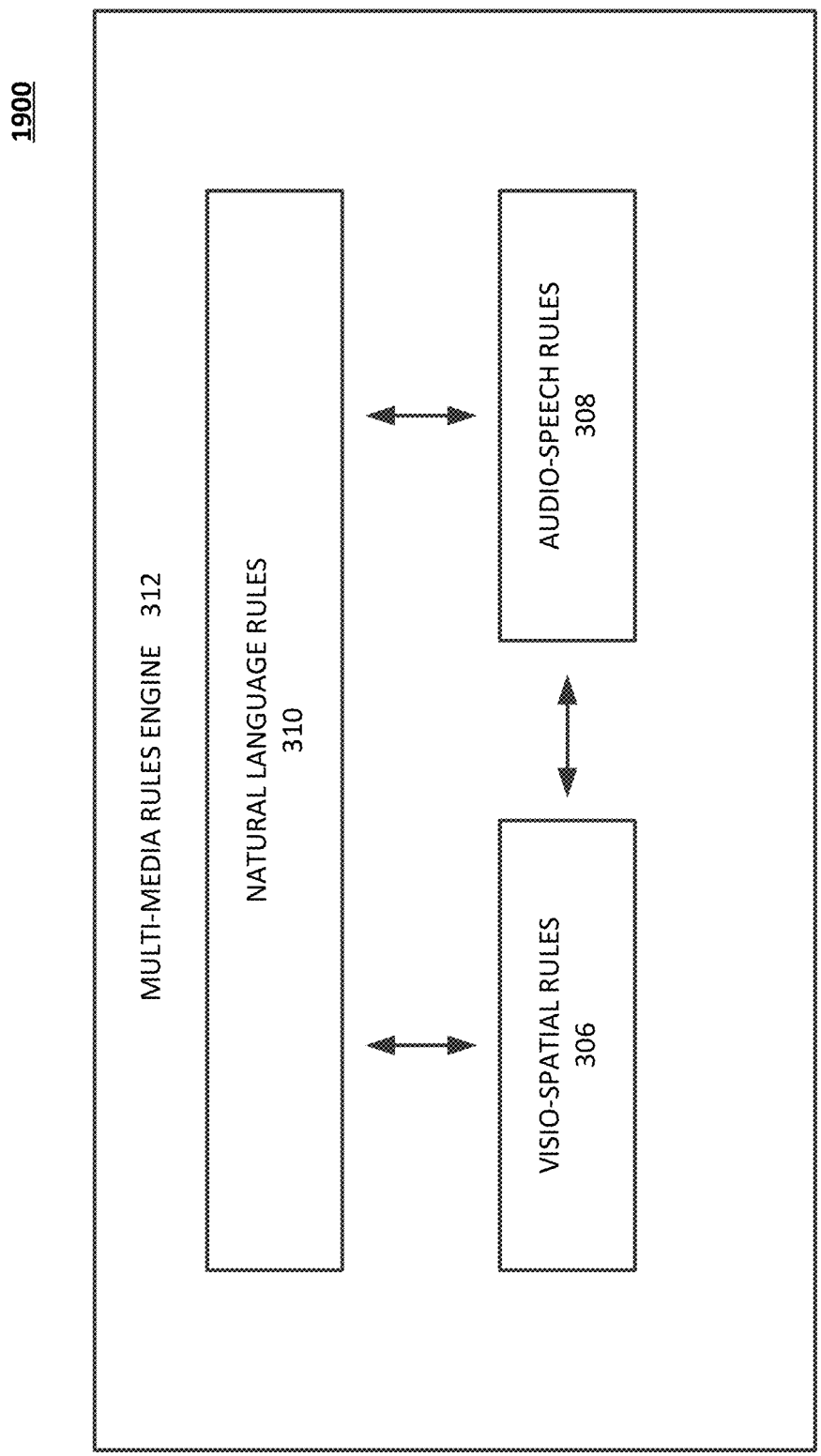
FIG. 19 is a block diagram of a multi-media rules engine in accordance with an exemplary aspect of the disclosure.

FIG. 19 is a block diagram of the multi-media rules engine. Textual, visio-spatial and audio data are compared and re-processed as Multi-Media Rule Suggestions and sent back to the Natural Language Rules Engine (310), Visio-spatial Rules Module (306), and Audio-Speech Rules Module (308).

Subsequent audio or visual input exhibiting similar, opposite, partial-matching or exhibiting an otherwise mathematically significant ratio or relationship in audio or visual signals and patterns will receive tags indicating likelihood of the Emotio-Cognitive class.

Comparison of likeness, differences, opposites, and other measurements of each Multi-Media Rule Engine's 312 Rules and suggested rules will improve the rule-suggesting ability, and highlight modular components of each rule.

In one embodiment, HUNCHes are used as hooks, allowing the system to analyze surrounding text, suggesting potential new rules back to the Multi-Media Rules Engine (312). Dimensional patterns must match Positive and Negative Dimensions or be noncontradictory to the rule pattern.

In particular, the HUNCHes are non-construction based partial pieces (such as 1-2 words, or partial phrases), which carry their own dimensions. Feeding these into the system 300 allows the neural models 320 to "match" these partial-dimensional patterns and use them as hooks for finding indicators of emotion. In an example, an ANGER rule lies undiscovered, but has Ego+1, Impatience+1, Force+1, etc. A hook (like "I won't") may only have Ego+1 and Force+1, but if it looks enough like it could fit with anger, the surrounding text will be examined. To do this, it must have 0 contradictory dimensions, and it must have its existing dimensions matched. This allows permutations of rules to be detected (where both are true), or potentially new rules (where not contradictory, but where the dimensional profile looks enough like anger). Through this technique, a new ANGER construction is found such as "I [won't/am not going to/am not gonna] take it ["one more time", "again", "anymore", "at all" ], etc., which might distill down to a rule like "[1P PRON]+([AUX VERB]+[NEGATION]+(("GO-ING")+[INFINITIVE-VERB] or [FUTURE-VERB])+((D-OBJECT-PRON))*+[WordList: Time-Phrase]+"!"", with asterisked portions optional, yielding, for example:

I'm not going to take it anymore!
I'm not going to serve you again!
We will not bow anymore!

For some emotions and some dimensions with respect to a given emotion two or more values may be acceptable. For example, anger can be blunt or nuanced so could receive either score.

In some embodiments, depending on the emotion and the dimension, more than one value may be acceptable. For example, Anger can (and must be either) ego-neutral or ego-positive. In other cases, it must be one valence for a dimension. For example, Anger must be forceful; anger must be specific. Consecutive HUNCHes together might match an emotion dimensional array. They also might not, if emotion shifts.

Figure 20:
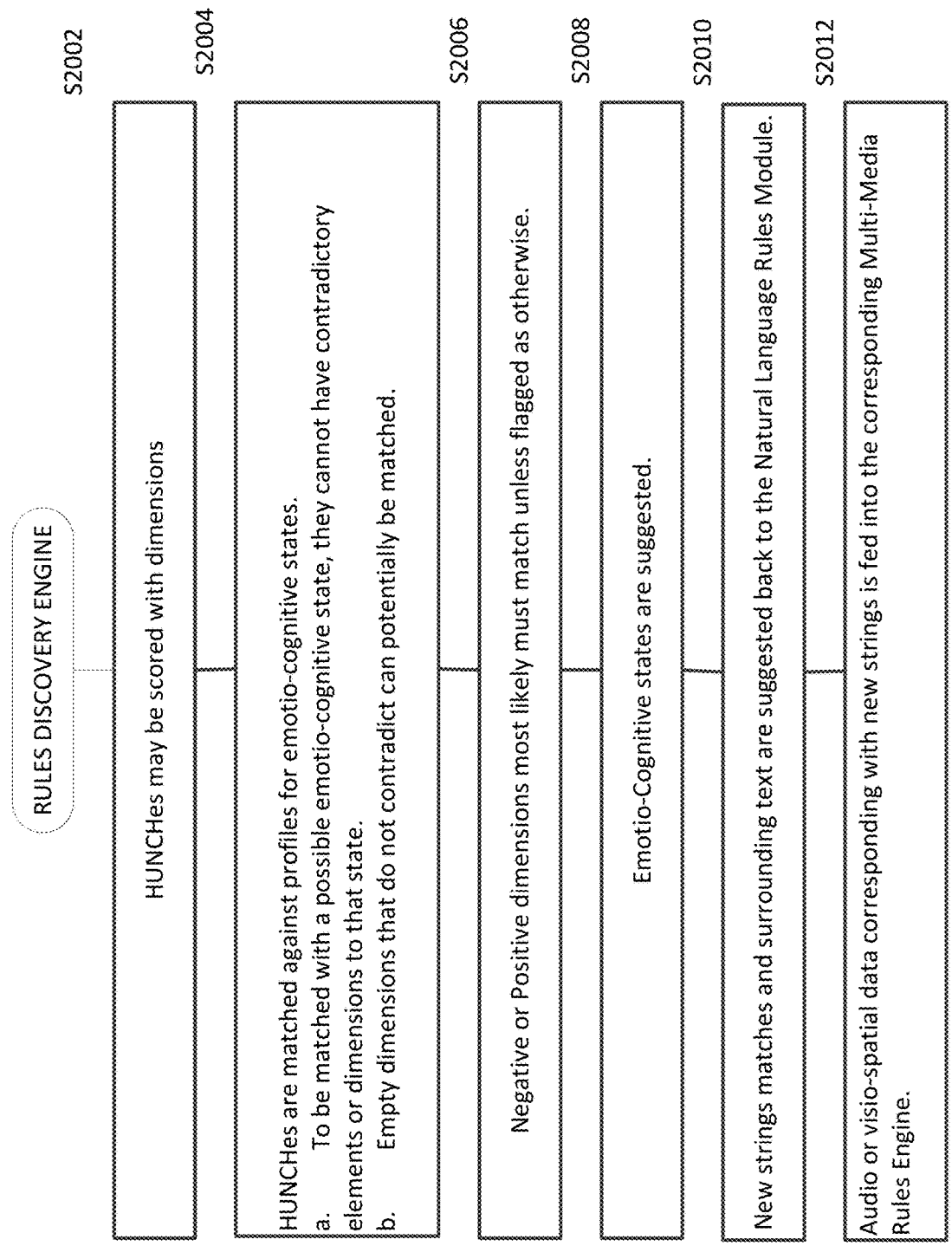
FIG. 20 is a flowchart for a rules discovery engine based on HUNCHes in accordance with an exemplary aspect of the disclosure.

FIG. 20 is a flowchart for a rules discovery engine based on HUNCHes in accordance with an exemplary aspect of the disclosure. The process is performed in the rules discovery engine 326.

In S2002, dimensions associated with HUNCHes may be scored.

In S2004, HUNCHes are matched against profiles for emotio-cognitive states. To be matched with a possible emotio-cognitive state, they cannot have contradictory elements or dimensions to that state. Empty dimensions that do not contradict can potentially be matched.

In S2006, Negative or Positive dimensions must likely match unless flagged as otherwise.

In S2008, Emotio-Cognitive states are suggested.

In S2010, new string matches and surrounding text are suggested back to the Natural Language Rules Module 306.

In S2012, audio or visio-spatial data corresponding with new strings is fed into the corresponding Multi-Media Rules Engine 312.

Figure 21A:
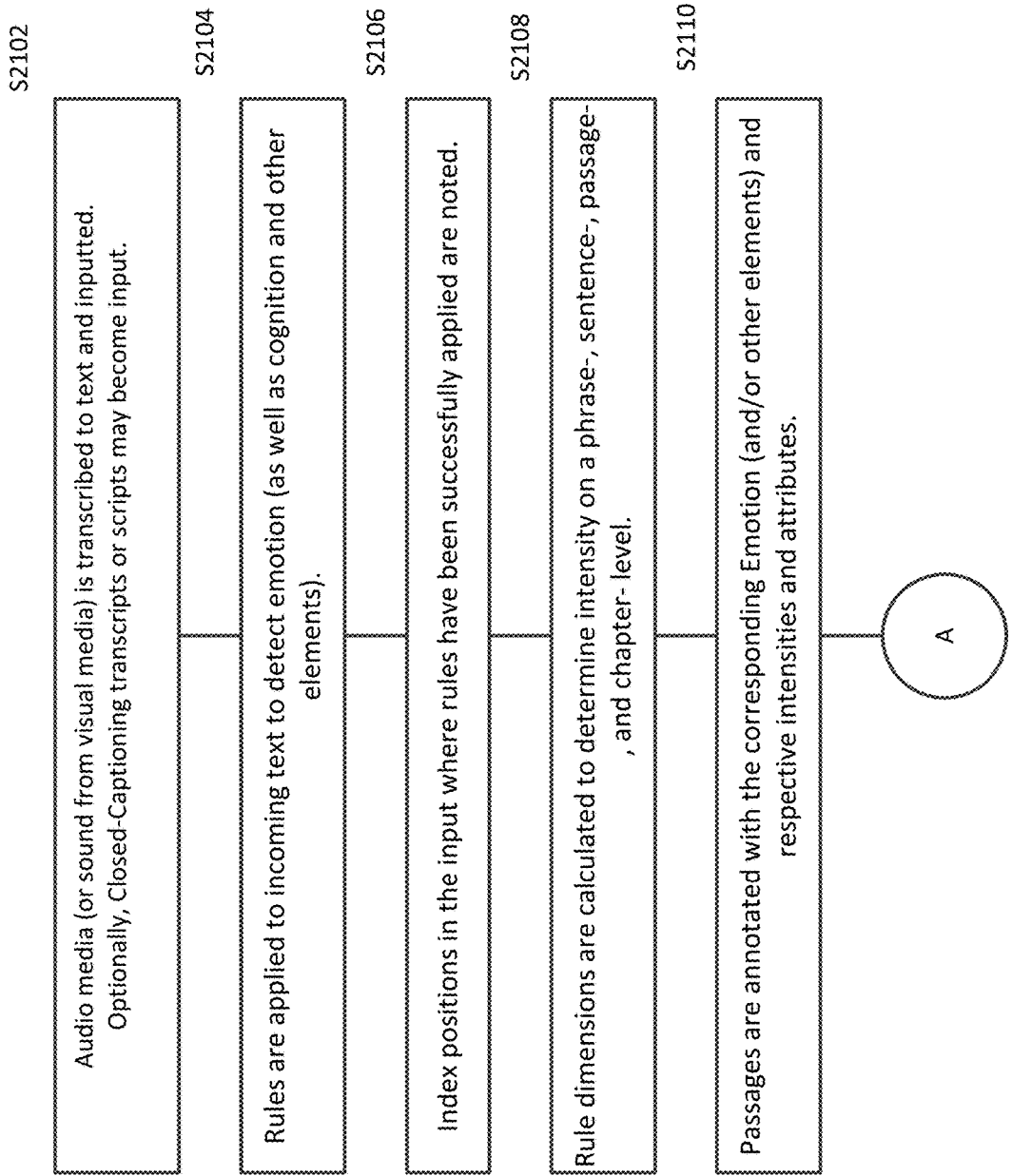
FIGS. 21A, 21B is a flowchart for rule discovery in audio media in accordance with an exemplary aspect of the disclosure.
Figure 21B:
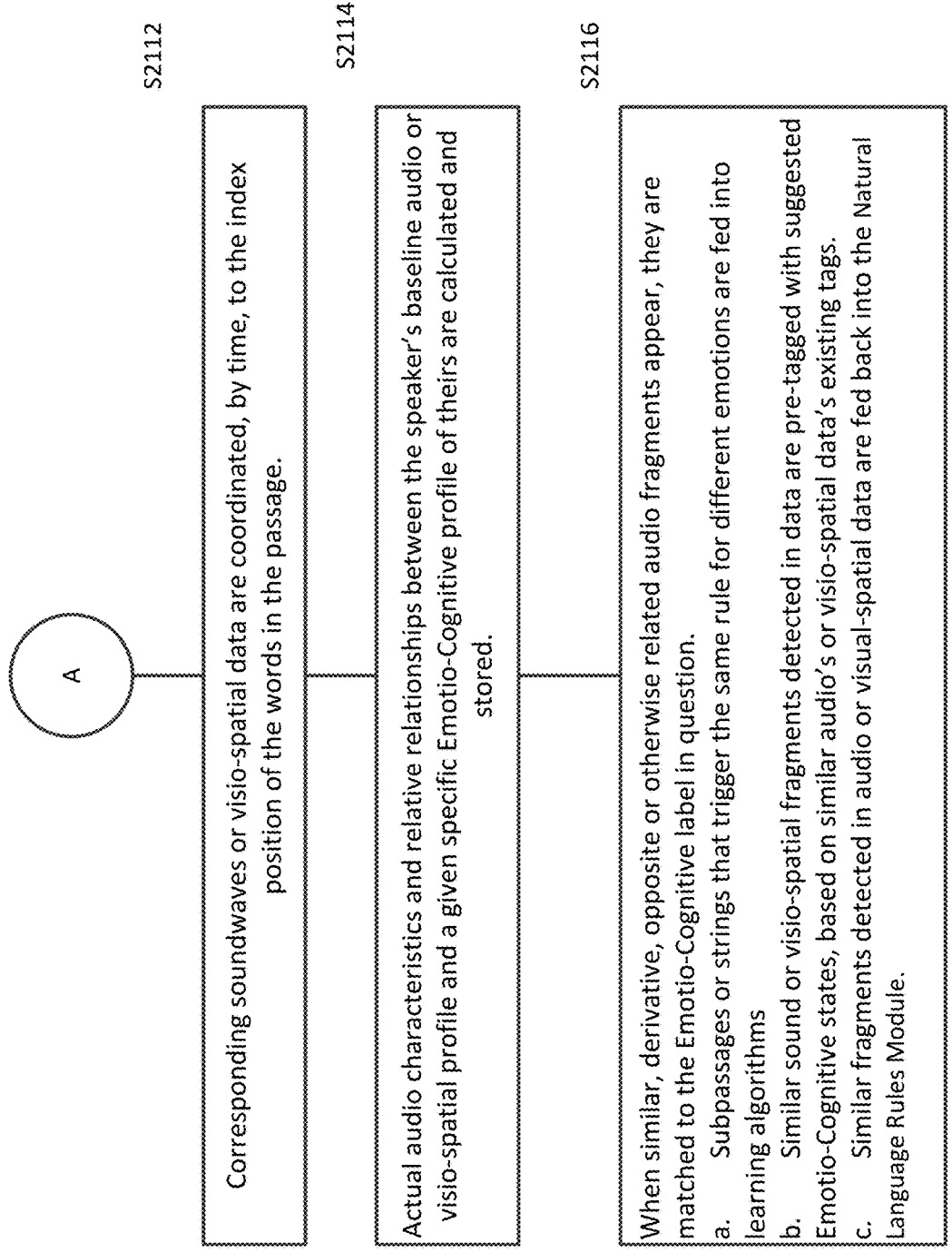

FIGS. 21A, 21B is a flowchart for rule discovery in audio media in accordance with an exemplary aspect of the disclosure.

In S2102, audio media (or sound from visual media) is transcribed to text and inputted. Optionally, Closed-Captioning transcripts or scripts may become input. In some embodiments, gasps, noises, gestures, and other non-textual audio may be transcribed as annotations in order to capture more features of the audio media.

In S2104, rules are applied to incoming text to detect emotion (as well as cognition and other elements).

In S2106, index positions in the input where rules have been successfully applied are noted In S2108, rule dimensions are calculated to determine intensity on a phrase-, sentence-, passage-, and chapter-level.

In S2110, passages are annotated with the corresponding Emotion (and/or other elements) and respective intensities and attributes.

In S2112, corresponding soundwaves or visio-spatial data are coordinated, by time, to the index position of the words in the passage.

In S2114, actual audio characteristics and relative relationships between the speaker's baseline audio or visio-spatial profile and a given specific Emotio-Cognitive profile of theirs are calculated and stored.

In S2116, when similar, derivative, opposite or otherwise related audio fragments appear, they are matched to the Emotio-Cognitive label in question. Subpassages or strings that trigger the same rule for different emotions are fed into learning algorithms. Similar sound or visio-spatial fragments detected in data are pre-tagged with suggested Emotio-Cognitive states, based on similar audio's or visio-spatial data's existing tags. Similar fragments detected in audio or visual-spatial data are fed back into the Natural Language Rules Module 306.

Figure 22:
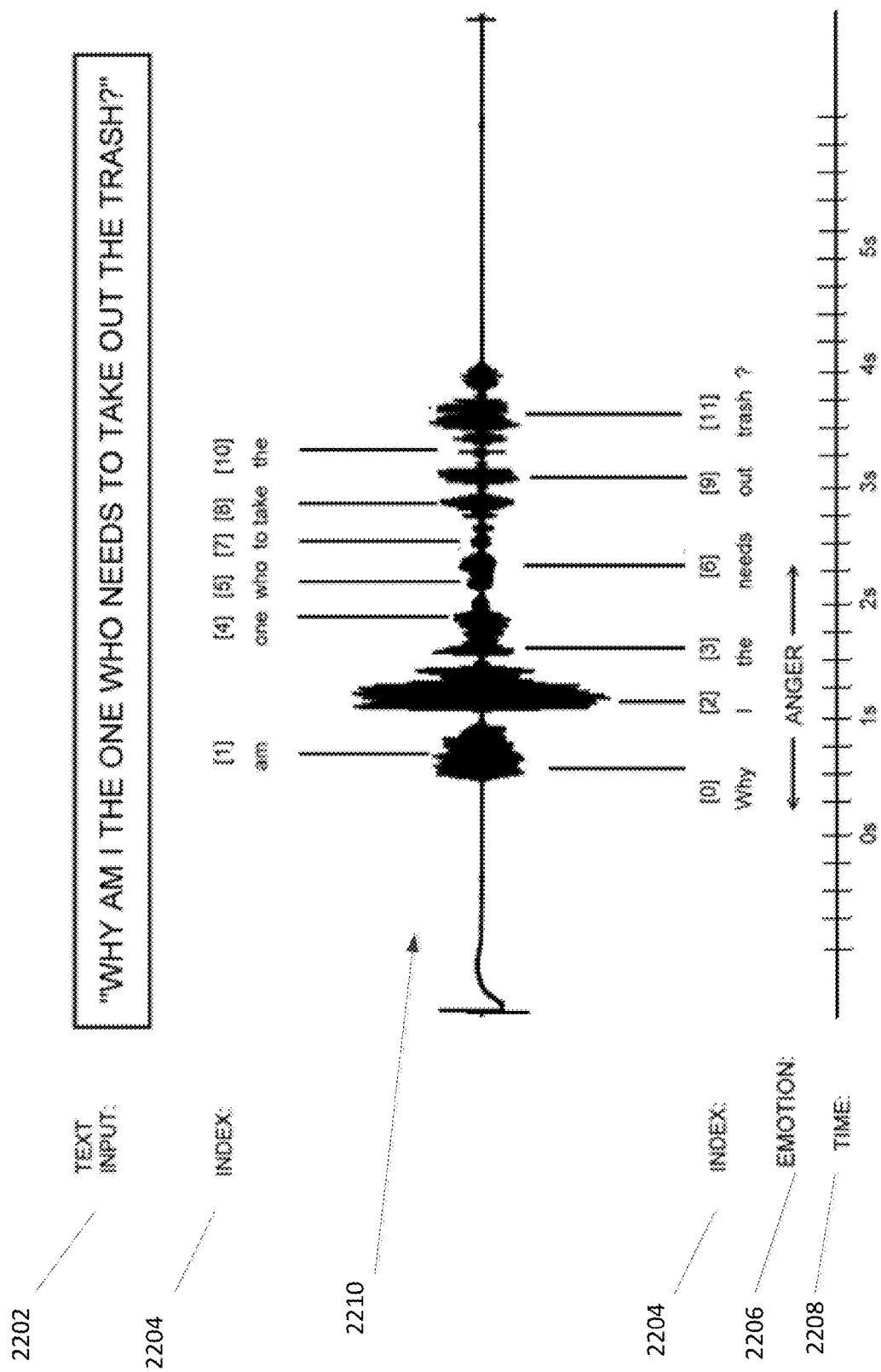
FIG. 22 is a graph of a speech signal pattern.

FIG. 22 is a graph of a speech signal pattern. In one embodiment, the speech signal pattern 2210 for a text input 2202 is indexed 2204 with the text input 2202 and is used to mark the beginning time and ending time (2208) for an emotion 2206.

Emotio-Cognitive Dynamic Display

Historically, certain subsets of the population have experienced various barriers to understanding emotional, cognitive, social, belief-based, interpersonal, or metacognitive, meta-emotional, or decision-making cues or dynamics in spoken or written text. In particular, people who are non-neurotypical (e.g., neurodivergent), with conditions such as autism, encounter problematically high rates of misunderstanding or missing social cues, emotions, and other dynamic elements present in the language. Non-native speakers of a given language may also encounter these difficulties. Media consumed by these populations can be confounding, confusing, misleading, and sometimes lead to disconnection, interpersonal conflict or alienation, shunning, and isolation when social norms are not understood and/or transgressed. Enjoyment of media may also be reduced, or less able to be spoken about for social bonding reasons. Entertainment companies can also lose or experience reduced viewership because audiences do not pick up on the emotional, interpersonal, belief-based, or cognitive dynamics at hand.

Analyzed and annotated subtitles can be fed into machine learning algorithms, for greater efficacy as new situations, dynamics, emotions, cognitive states and social aspects, currents, and dynamics evolve or are introduced. Theory of mind modules can be updated with additional iterations, to adjust to a given society, gender, religious, belief, age, topic, or culture or subculture, for accuracy.

Training data can be partially automated due to the robust information retrieved and matched to incoming media.

Media can be created using the training data, and written, collected, spliced, compromised or mimicked using the annotations on prior data.

Training data can be auditory, visual, textual, multisensory, or a combination of all types.

One type of training data includes the GoEmotions dataset, with the following modifications: Elimination of the Desire class; Elimination of the Neutral label, and instead, the use of the neutral label in deriving a Surety Score of: 1−Neutral probability score=Surety Score.

Training data is sourced from locations where sentiment such as but not limited to emotions, cognitions and other dimensions are necessarily or with above-threshold necessity logically required to be the case, and/or where the author self-proclaims their own emotion, effectively providing tags, and allowing for empirical labels.

An embodiment of the system 300 for automated classification of emotion is an Emotio-Cognitive Dynamic Display. The dynamic display can insert subtextual data of emotion in real time which allows neurodivergent users to learn and refine their social, emotional, interpersonal and theory of mind skills as they go.

The natural language rules engine 306 is configured with rules consisting of constructions, baseds, high-use, and/or permutable phrases allowing for quick determination of linguistic patterns in textual information made available by subtitles. Hashtags are broken up by contextual, and corpus, unigrams and other present n-grams derived from the input, instead of merely made available via lexicon(s), providing for more accurate, more relevant natural language processing and sentiment analysis. Similar, partial or opposite dimensional patterns are used for detection of sentiment. Rules are created to encode dimensions that can be used to detect mental health symptoms in each rule-triggering construction.

The emotio-cognitive engine 314 is configured to score subcomponents ("dimensions") for each rule allowing for fast and increasingly-accurate recognition of motivation, influence, emotion and cognition and similar subcomponents which aggregate in distinct patterns and combinations to identify transient and enduring emotive, cognitive, belief-based, opinion-centered, social and personality states. Emotions are deduced from the "shape" of the dimensions. Features of emotions can include the vector of the dimensions, the values of the dimensions, and the difference from or similarity to derived calculations from these parts.

The emotio-cognitive tagging engine 318 is configured for tagging and tracking of development of subtextual information over the course of subtitles and speech using the emotional, cognitive, belief, motivational and opinion state subcomponents. Once emotions are tagged, Aggregate Emotio-Cognition Ensemble Classifier 328 tags meta-emotional states, shifts, and combinations based on emotional patterns.

The rules discovery engine 326 is configured to identify, utilize, deduce from and infer gapped emotional states, trends, dimensional transitions, and other sentimental states and shifts to suggest potential new rules, which are then fed back into the system 300. Emotional patterns and Meta-emotional shifts, states, and combinations are deduced from gaps within patterns of emotion, cognition, or other sentimental components. The rules discovery engine 326 is configured with affective logic that is used to deduce missing sentimental states and shifts in the data, or to solve semantic, cognitive, emotio-cognitive or otherwise sentimental ambiguities. The rules discovery engine 326 is configured to control training of the machine learning models engine 320 on the "edge" of the classes, such as between near-emotional states, like Grief and Sadness, or Sadness and Anger, for more adept, finer, and faster differentiation.

The display 210 is configured to display juxtaposed subtextual cues against visual and auditory (auditory tone and speech) data to enable richer information, and situational awareness. Subtextual data is displayed to inform users and viewers and augment and/or clarify social situations and complex emotional and cognitive states depicted or described in the media.

The rule discovery engine 326 is configured to work with the machine learning models engine 320. Analyzed and annotated subtitles can be fed into the machine learning models engine 320 as new situations, dynamics, emotions, cognitive states and social aspects, currents, and dynamics evolve or are introduced. Training data can be obtained from information retrieved and matched to incoming media. Training data can be auditory, visual, textual, multisensory, or a combination of all modes.

In one embodiment, training data includes the GoEmotions data set. In the embodiment, the GoEmotions dataset is modified by deleting the Desire class. The Neutral label is replaced with a Surety Score that is derived from the neutral label, as: 1-Neutral probability score=Surety Score.

In some embodiments, training data is obtained from sources where sentiment such as but not limited to emotions, cognitions and other dimensions are necessarily or with above-threshold necessity logically required to be the case, and/or where the author self-proclaims their own emotion, effectively providing tags, and allowing for empirical labels.

FIG. 23 is a flowchart for a method of real time emotion classification in a stream of video/audio in accordance with an exemplary aspect of the disclosure. The method is performed with a display device, including a tablet computer, smartphone, smart TV, that receives streaming audio and/or video, and that includes its own built-in computer with memory.

In S2302, a scene from a movie or television show or streaming show or captured theatre play or animated video source is received together with coordinated textual transcription.

In S2304, rule matching of the textual data is performed by the rule-based engine 306 emotio-cognitive engine 314, intensity rating sensor 316, and emotio-cognitive tagging engine 318, which tags emotional, cognitive, and other such states, with intensity ratings, in the textual transcription.

In S2306, the aggregate emotio-cognition ensemble classifier 328 determines contextual clues based on word co-occurrence, discursive elements, and topic elements.

In S2308, the emotio-cognitive sensor 316 optionally marks individual strings or n-grams with trinary dimensional scores.

In S2310, the visio-spatial rules engine 310 and audio-speech rules engine 308 detect and enter augmented information (AugI) and situational elements (SE) apparent in visual data or tone elements apparent in auditory data into a separate, but time-coordinated, source for the media.

In S2312, the emotio-cognitive sensor 314 performs juxtaposition (coordination and divergence, and degree of each) from the context-oriented semantic information (contextual clues) and AugI and SE data, creating context scores for each scene.

In S2314, bracketed emotional data is returned inline and inserted into the textual transcript for display in the display device 210 so that the viewer may have an easier time correctly identifying emotional, cognitive or social elements of the media.

Figure 24:
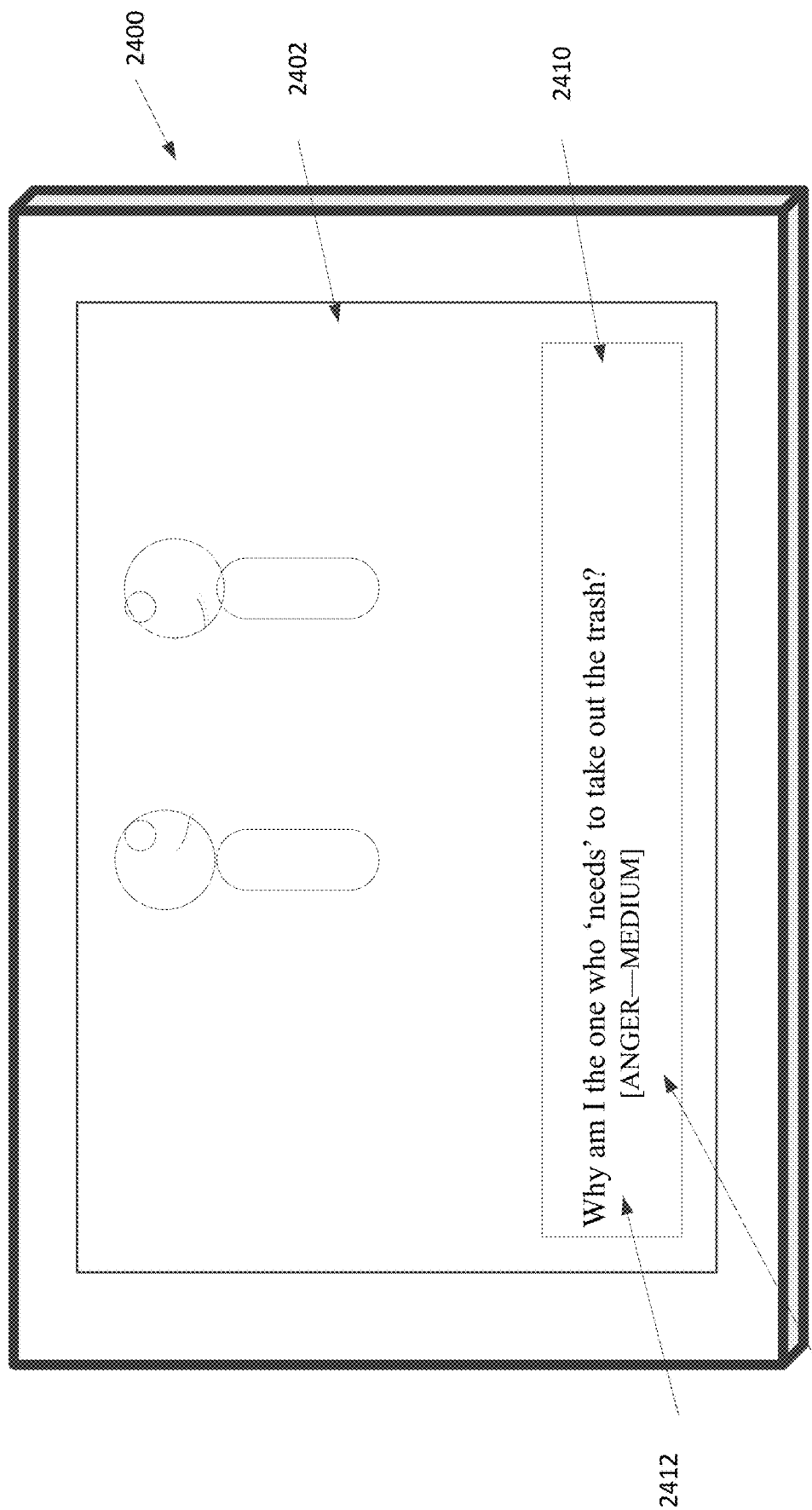
FIG. 24 illustrates a display device in accordance with an exemplary aspect of the disclosure.

FIG. 24 illustrates a display device in accordance with an exemplary aspect of the disclosure. An example display device 2400 includes a display screen 2402 for displaying a scene from a movie or television show or streaming show or captured theatre play or animated video source together with coordinated textual transcription. In this example screen, bracketed emotional data 2414 (e.g., Emotion-Intensity pair) is returned inline and inserted into the textual transcript 2414 and displayed in the display device 2400.

Borderline Personality Disorder Soothing Device

Figure 25:
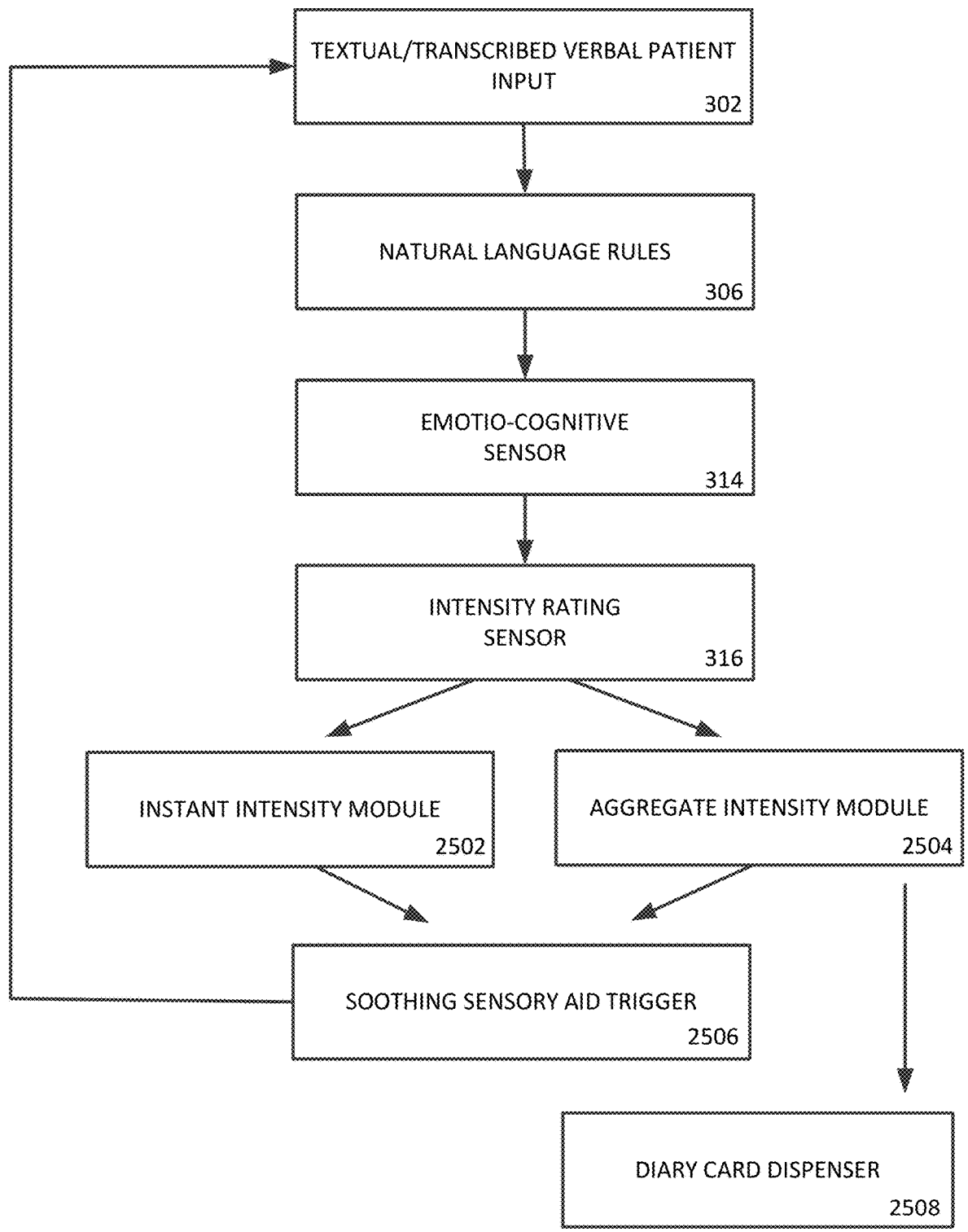
FIG. 25 is a system diagram of adaptive operation of the emotion classification system in accordance with an exemplary aspect of the disclosure.

FIG. 25 is a diagram for the emotion classification system with sensory distraction in accordance with an exemplary aspect of the disclosure.

Borderline Personality Disorder (BPD) is a mental health disorder that impacts the way one thinks and feels about oneself and others, causing problems functioning in everyday life. t includes self-image issues, difficulty managing emotions and behavior, and a pattern of unstable relationships. Treatment for BPD includes learning to manage emotions that feel uncomfortable. Disclosed embodiments include a peripheral device for giving feedback based on certain emotions and pattern of emotions, especially intensity of emotion.

A patients diagnosed with Borderline Personality Disorder (BPD) can be provided with a microphone equipped device or an input device that can accept input from a keyboard, other text input device, such as a voice recorder with transcription, or device with a text input function, such as a touchscreen equipped device having a text input screen. Speech signals may be converted/transcribed into text. Text may be directly input (302) to a device. The device is preferably a portable/mobile computing device that the patient may carry. In some embodiments, the portable/mobile computing device may be a device that facilitates digital communication with a cloud service.

The textual input is processed by the Natural Language Rules Module (306), which then provides Emotion labels, and passes the input to the Emotio-Cognitive Sensor (314).

The Intensity Rating Sensor (316) computes dimensions for each input and assigns an objective intensity rating.

Running averages and aggregate scores are computed in the Aggregate Intensity Module (2504).

Instantaneous intensity scores are computed in the Instant Intensity Module (2502).

When the running Negative Emotional Intensity in the Aggregate Intensity Module (2504) reaches a high enough threshold, the system may optionally proactively dispense a sensory-soothing aid (2506) via a peripheral device, configured for Dialectical Behavioral Therapy (DBT), in order to create a sensory soothing distraction for the patient, including, but not limited to: Dispensation of spicy candies, Misting of scented spray, Vibration of Bluetooth bracelet, Heating of Bluetooth wristband.

When any given data point in the Instant Intensity Module (2502) reaches a Negative Emotional Intensity over a Danger threshold, the system proactively activates periphery device 2506 to create a sensory distraction.

Intensity monitoring of language or speech resumes via both the Intensity Rating Sensor (316) and the Emotio- Cognitive Sensor 314. When aggregate or data-point intensity reaches a first threshold, a different randomized sensory soothing distraction is activated.

Once the Aggregate Intensity Module (510)'s running average and the Instant Intensity Module's (2504) ratings have not for 30 or more minutes, a diary card is dispensed (2508) by the central unit for the patient to fill out and record the experience, for personal or therapeutic use.

In other embodiments, the emotion classification system with sensory distraction has application beyond BPD. Optionally, a user overcoming their addiction to alcohol, drugs or compulsive behavior is monitored in an aftercare rehabilitation program or sober living home, for Emotio-Cognitive signs preceding, or of, relapse, and provide textual or transcribed input (302) to a device. Optionally, a worker's or manager's professional communications are monitored for signs of particular emotio-cognitive states, such as stress or anxiety, and inputted (302) to a device. Optionally, when the running Negative Emotional Intensity in the Aggregate Intensity Module (2504) reaches a high enough threshold, the system alerts the facility, rehabilitation program, or sober living home, or the employer that the user is at risk of relapse, or extreme stress or anxiety.

Figure 26A:
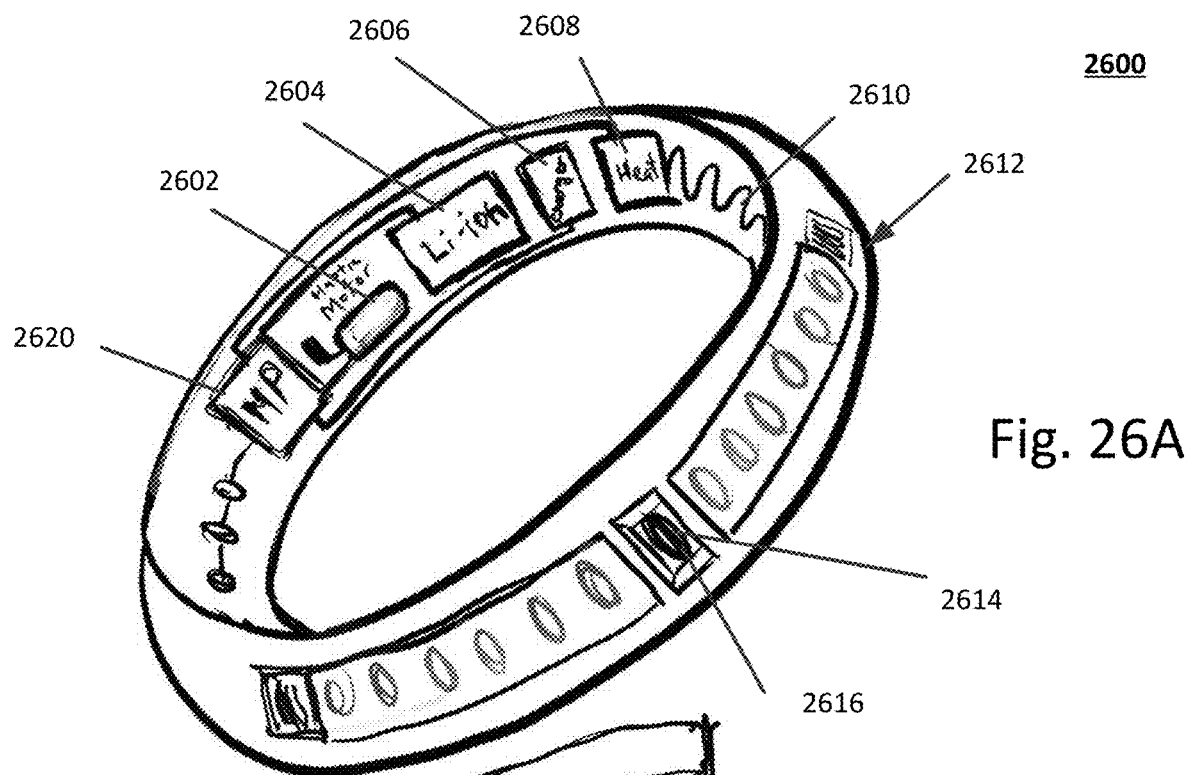
FIGS. 26A, 26B, 26C is a schematic diagram of an electronic bracelet in accordance with an exemplary aspect of the disclosure.
Figure 26B:
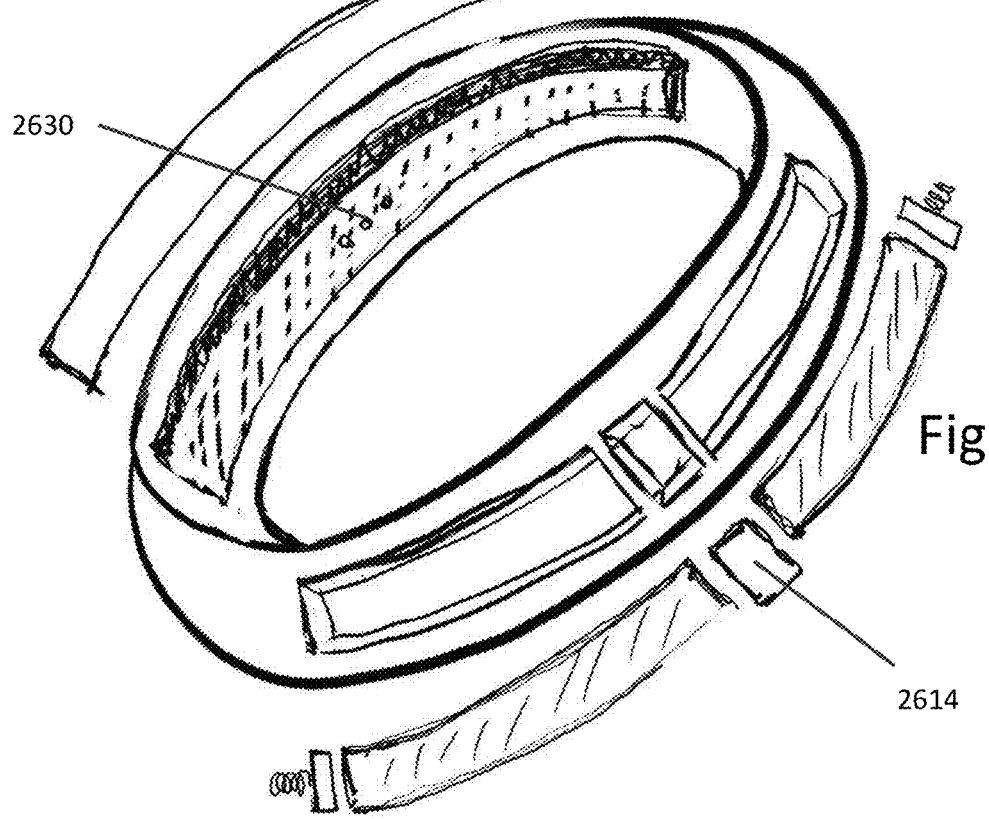
Figure 26C:
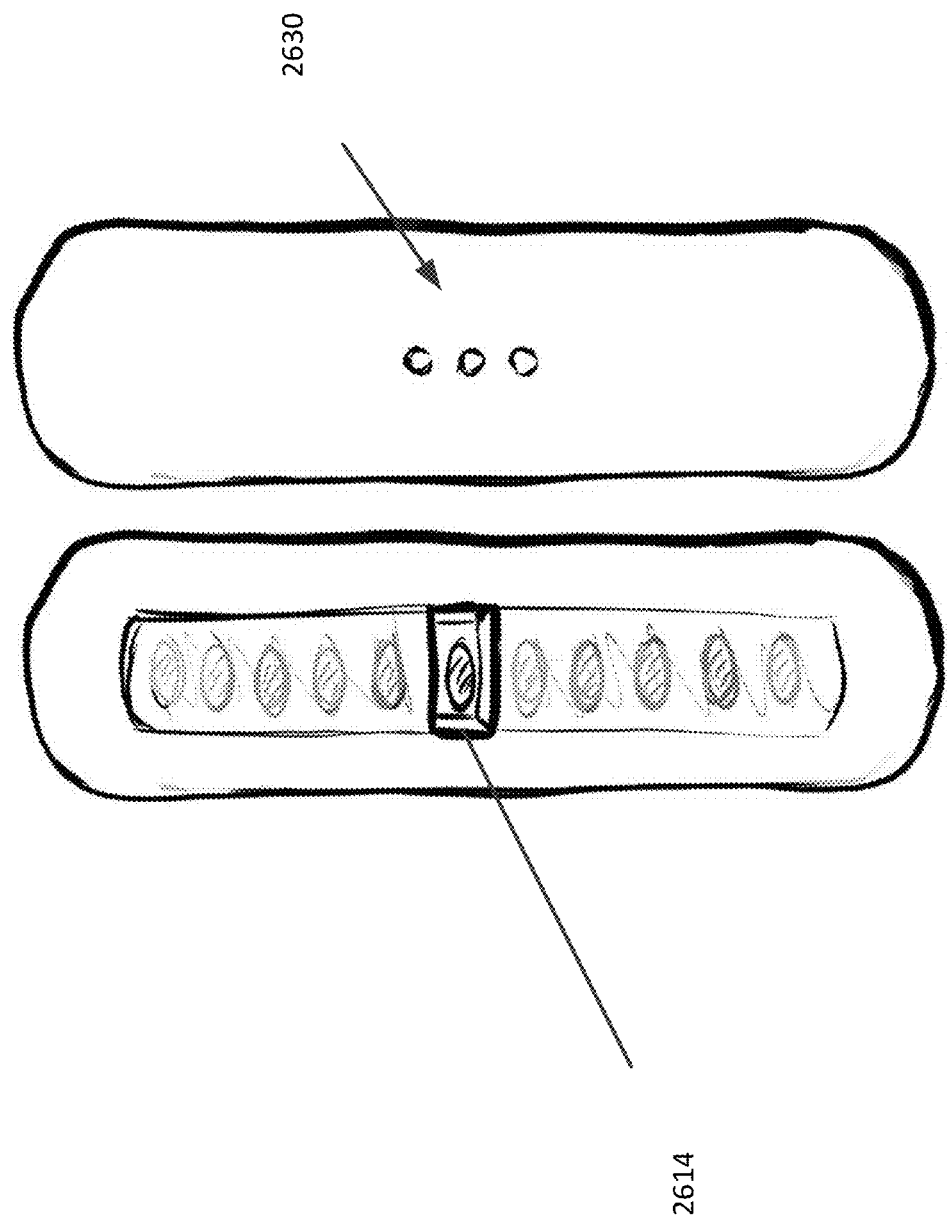
Figure 27:
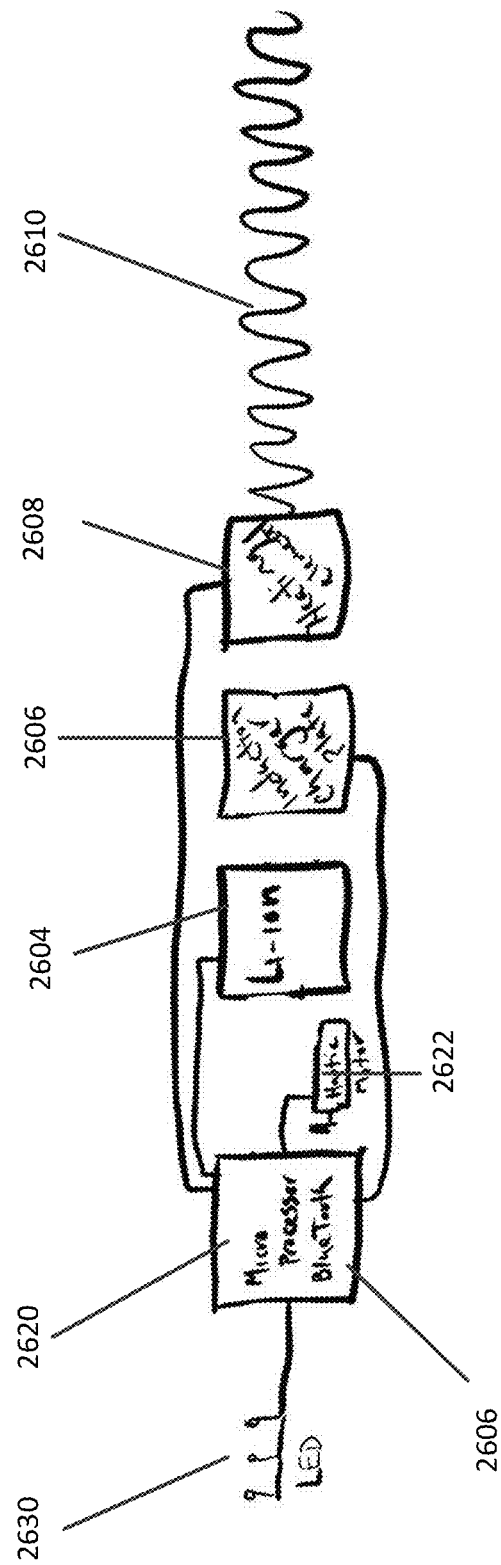
FIG. 27 is a circuit diagram for an electronic bracelet in accordance with an exemplary aspect of the disclosure.

FIGS. 26A, 26B, 26C is a schematic diagram of an electronic bracelet in accordance with an exemplary aspect of the disclosure. The electronic bracelet 2600 may be in the form of a ring 2612 having embedded electronic components.

Wires:

The wires 2610 are a bundle of multiple insulated wires. Individual wires are either positive '+' or negative '−'. The wires 2610 are preferably nichrome (nickel chromium), but may be made of other wire materials.

The bracelet 2612 may include an embedded communications chip (connected to a microprocessor chip 2620), configured for wireless communication. The wireless communication is preferably a short range communication for transmitting and receiving signals from the portable/mobile device. In one embodiment, the communication chip performs wireless communications using Bluetooth, or Bluetooth low energy (BLE).

A sliding window feature 2614 is glass or plastic. The sliding window 2614 exposes a dispenser 2616, which is single aperture. The sliding window 2614 is motorized with a micro solenoid step motor 2602. (<5 mm).

The device 2600 is powered by an embedded microprocessor 2620. The microprocessor includes seatings for the wires and components using assembly board-type technology.

A micro electromagnetic eccentric motor 2622 is an actuator that generates vibration (imbalanced load).

A copper plate 2608, seated in silicone, provides heat.

The device is powered by a Lithium-ion rechargeable battery 2604. The rechargeable battery 2604 has an associated recharging interface 2606.

Indicator lights 2630 on the band 2612 exist for pairing with the portable/mobile device.

The band 2612 is translucent and can change color via LED lights depending on the emotion detected. This may be useful for people with BPD experiencing aversive tension, in a heavily activated state, to communicate their emotions with caregivers or loved ones.

An adaptation of the device 2600 may also be useful for grounding people with PTSD amid panic attacks, and transmitting emotional information to loved ones and caregivers when triggered.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art.

Emotio-Cognitive Profiler

In an example embodiment, emotio-cognitive classification may be implemented as a profiler.

Text input is spoken or otherwise entered into the Natural Language Rules 306 for analysis. Input may be about the user, another person, or a topic. Optionally, a user may video-capture themselves answering randomized job prompts. Optionally, OCR or audio transcription transcribes written and video or audio encapsulated (respectively) textual information to plain text.

Text is analyzed by the Emotio-Cognitive Sensor 314 for sentimental content.

Emotio-cognitive sentiment is labeled by the Emotio-Cognitive Tagging Engine 318 after classification.

The intensity of sentiment is calculated via dimensions within the Intensity Rating Sensor 316.

A profile is generated with Personality Traits, Expression Traits, Cognitive Traits, and Emotional Traits as well as Values and Biases, within the Emotio-Cognitive Profiler.

Demographic information is associated with profile information in the Emotio-Cognitive Profiler.

The Aggregate Emotio-Cognition Ensemble Classifier 328 makes predictions about the type of candidate who will make a strong fit for the date, job, or jury. Optionally, the user inputs, such as by survey or questionnaire, information about the type of personality traits, values, cognitive traits, emotional traits, values and decision points their ideal candidate would exhibit.

Recommendations are made to dating site users, jury consultants, or hiring managers to recommend a given person as a match, rating desirability and fit.

The profiles compiled by the Emotio-Cognitive Profiler are retained and stored for future use by the Machine Learning Models Engine 320.

Emotio-Cognitive Informed Textng/Communicaton

In an example embodiment, emotio-cognitive classification may be implemented as a pre-text application, including, among other things, phone banking, or text banking.

The user submits textual or transcribed input into the system for emotio-cognitive guidance to inform the user about healthy, empathetic, positive, and socially- and/(sub)culturally-aligned communication techniques and psychology.

Optionally, the relationship in question may be: sales relationship; customer service relationship, workplace relationship, academic relationship; counseling/coaching relationship; romantic relationship; friendship; family relationship; former or proposed relationship; estranged relationship; relationship in crisis; acquaintance relationship; or other human relationship.

When unhealthy, inappropriate, insensitive, confusing, or perspective-limited responses are detected in the user or the user's text, the user is prompted to develop their communication skills to learn about stronger communication approaches, via games, modules, tutorials or other teaching devices. Whether or not the user opts for a learning game or module, the user is asked if they would like to add more context to the situation.

The user is asked if they would like to try the communication again.

If the user chooses to add context, they can answer a series of questions that help assess emotio-cognitive states and the emotional or social situation. If the user declines to provide extra context, the user can opt to be asked further questions to assess his or her own emotio-cognitive state.

Optionally, users can select from a list of worries, issues, problems and hopes for the communication or relationship.

The user is given the opportunity to change their communication technique and input a new communication that incorporates the user's new knowledge and awareness, or reflects their changed emotio-cognitive state.

Users are prompted to start fresh.

Dynamic/Adaptive Embodiment

Spontaneous user textual or transcribed input is entered into a computing device, app, gaming console, phone, or tablet.

Text goes to the Pre-Processing Engine 304 and analyzed by Natural Language Rules 306 and then analyzed by the MultiMedia Classification Engine 312.

Overtly stated (expicit) and subtextually detected (implicit) emotio-cognitive states are assessed in the Emotio-Cognitive Sensor 314 and degree of mental states are scored in the Intensity Rating Sensor 316.

User inputs receive labels in the Emotio-Cognitive Tagging Engine 318.

The system provides a crafted, selected, generated, edited, or otherwise transformed response and/or adapted to the user's emotio-cognitive state, providing a customized, interactive, discursive experience for the user. Optionally, the discourse may involve more than one computer-generated and/or guided bot or character. Optionally, the discourse may occur during the course of a traditional, virtual reality, or augmented reality video game. Optionally, the discourse may involve one or more additional human agents. Optionally, the discourse may involve a therapeutic bot providing psychotherapeutic-, counseling-, crisis- or sobriety help to the user or groups. Optionally, the discourse may involve a virtual friend or assistance providing companionship or help to the user. Optionally, the discourse may involve one or more automated sales or customer support bots.

Optionally, environmental controls such as complexity, difficulty, volume, speed, color scheme, interventions, plotlines, mini-games and/or side quests, options, questions, characters, alerts, commentary, dialogue, capacities or offered choices, and other such customizations and custom activities adapt with user response to the most recent and aggregate bot-driven language replies.

Past responses from the user/s are stored in a database, along with respective iterated prompts, for future reference during current and future user sessions.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosure. For example, this technology may be structured for cloud computing whereby a single function is shared and processed in collaboration among a plurality of apparatuses via a network.

What is claimed is:

1. A method, implemented by processing circuitry, for detecting a psychological affect in a natural language content with an adaptive rule-based engine, the method comprising:
   receiving, via an input device, the natural language content as a textual input;
   preprocessing, by the processing circuitry, the received natural language content;
   searching, by the rule-based engine, for matches between (1) a plurality of linguistic rules for a corresponding plurality of emotion-cognitions, and (2) components of the preprocessed natural language content, wherein each of the plurality of linguistic rules has an associated one or more human dimensions;
   activating, by the rule-based engine, the matched linguistic rules, and evaluating the one or more human dimensions associated with each of the matched linguistic rules;
   scoring, for each linguistic rule of the matched linguistic rules, each of the one or more human dimensions to obtain a vector of one or more dimension scores for the corresponding emotio-cognition of the linguistic rule, and storing the vector in a memory;
   aggregating, for each linguistic rule of the matched linguistic rules, the obtained vector of one or more dimension scores stored in the memory to obtain a corresponding intensity indication for the corresponding emotio-cognition of the linguistic rule;
   determining a particular emotio-cognition satisfying a predetermined criteria, based on the obtained intensity indications;
   displaying, by a display, the received natural language content together with the determined particular emotio-cognition and the corresponding intensity indication of the particular emotio-cognition;
   generating new linguistic rules by a machine-learning engine that performs supervised learning and unsupervised learning, wherein the generating comprises:
     receiving a plurality of natural language data items from a repository;
     normalizing and tokenizing the received plurality of natural language data items using a preprocessing engine to generate a plurality of preprocessed natural language data items;
     labeling the plurality of preprocessed natural language data items with an expressed emotio-cognition and an intensity of the expressed emotio-cognition;
     providing, in parallel, the plurality of preprocessed natural language data items to the unsupervised learning engine and the supervised learning engine;
     training, in parallel, the unsupervised learning engine and the supervised learning engine in multiple training epochs to identify, in the plurality of preprocessed natural language data items, a certain emotio-cognition, and determine an intensity value of the certain emotio-cognition, wherein each training epoch of the unsupervised learning engine provides rule suggestions to subsequent training epochs of the rule-based engine, and in each training epoch, the rule-based engine provides tabulation and scoring data to subsequent epochs of the unsupervised learning engine and the supervised learning engine; and providing an output representing at least one of the trained unsupervised learning engine and the trained supervised learning engine.

2. The method of claim 1, wherein the one or more human dimensions include one or more of emotional affects of ego, blame, conformity, sacredness, kindness, respect, time, favor, approval, sincerity, vulnerability, judgment, separateness, purpose, formality, minimization, specificity, force, action, agency, curiosity, clarity, intention, emphasis, energy, certainty, interest, engagement, shock or surprise, tension, speed, nuance, logic, paranoia, trust, distance, identification, esteem, objectification, attachment, empathy, or patience,
wherein each of the one or more human dimensions has a value being one of +1 for positive force, −1 for negative force, 0 for neutral force, and Ø for not present or not applicable, and
wherein the scoring step further comprises scoring, by the rule-based engine, each of the one or more human dimensions for all of the matched linguistic rules.

3. The method of claim 1, wherein the searching step further comprises:
detecting constructions based on the plurality of linguistic rules; and
evaluating the one or more human dimensions of each of the detected constructions.

4. The method of claim 3, wherein the detecting step further comprises:
detecting a presence or an absence of the constructions in the received natural language content having components related to the corresponding emotio-cognition of the plurality of emotio-cognitions.

5. The method of claim 3, wherein the detecting step further comprises determining a numeric value for one or more of:
a part of speech tagging or syntax rule,
a string matching rule that is exact, inexact, masked, or wildcarded,
a token proximity rule,
a punctuation rule,
a lemmatization rule,
a stemming rule,
a lexicon rule, or
a word lookup or dictionary-based rule.

6. The method of claim 5, wherein the step of determining the numeric value for the token proximity rule comprises accessing all tokens having a distance of fewer than n tokens from a specified point in the received natural language content, wherein n is a positive integer.

7. The method of claim 1, wherein the determining step further comprises, for each linguistic rule of the matched linguistic rules, comparing the obtained intensity indication to a threshold for the corresponding emotio-cognition to obtain a corresponding emotional intensity level.

8. The method of claim 1, further comprising determining, by the rule-based engine, a pattern of emotio-cognitions that includes the particular emotio-cognition, by concatenating with other emotio-cognitions detected by other of the plurality of linguistic rules, and identifying the pattern of emotio-cognitions as a dynamic emotio-cognition; and
tracking the particular emotio-cognition and the other emotio-cognitions together with associated components in a temporal sequence.

9. The method of claim 1, further comprising matching the one or more human dimensions to existing dimensional arrays, having wildcards or pattern skips, to identity new rules for the rule-based engine.

10. The method of claim 1, wherein the receiving step further comprises continuous reading of a streaming live video or animated video source together with coordinated textual transcription, and
the method further comprises
determining contextual clues based on word co-occurrence, discursive elements, and topic elements;
marking individual strings or n-grams with trinary dimensional scores;
detecting and entering further information apparent in visual data or tone elements apparent in auditory data into a separate, but time-coordinated, source for the video; and
performing juxtaposition from the contextual clues and further information, to create context scores for each scene in the video.

11. The method of claim 10, wherein the displaying step further comprises displaying the textual transcription in a manner that the particular emotio-cognition and the corresponding intensity indication are bracketed and inserted inline adjacent to components of the textual transcription.

12. The method of claim 1, further comprising:
detecting, by the rule-based engine, hook words or pairs of words in the received natural language content;
evaluating the one or more human dimensions associated with the detected hook word or pairs of words to determine when the hook words or pairs of words indicate a possible one of the emotion-cognitions;
when a possible emotio-cognition exists, extracting a predetermined window of words surrounding the hook words or pairs of words;
scoring, by the rule-based engine, the one or more human dimensions to obtain a particular vector of dimension scores for the hook word or pairs of words; and
when the particular profile of dimension scores is above a threshold, constructing a new rule for the possible emotio-cognition, based on the hook word or pairs of words and extracted surrounding words.

13. The method of claim 1, further comprising identifying an index position in the textual input at a position where one of the linguistic rules is matched.

14. The method of claim 13, further comprising annotating the natural language textual input with the particular emotio-cognition and the corresponding intensity indication at the identified index position.

15. The method of claim 1, wherein receiving, via the input device, the natural language content as a textual input, further comprises receiving, via the input device, the natural language content as an audio input and transcribing the audio input into text input, the method further comprising:
matching a fragment of the audio input with a stored linguistic rule for a similar sound fragment, and assigning the audio fragment with an emotio-cognitive label of the stored rule.

16. A method, implemented by processing circuitry, for detecting a psychological affect in a natural language content with a rule-based engine implemented by processing circuitry, the method comprising:
receiving, via an input device, the natural language content as a textual input;
searching, by the rule-based engine, for matches between (1) a plurality of linguistic rules for a corresponding plurality of emotio-cognitions, and (2) components of the received natural language content, wherein each of the plurality of linguistic rules have one or more human dimensions;

activating, by the rule-based engine, the matched linguistic rules, and evaluating the one or more human dimensions of the matched linguistic rules;

scoring, for each linguistic rule of the matched linguistic rules, each of the one or more human dimensions to obtain a profile of one or more dimension scores for the corresponding emotio-cognition of the linguistic rule;

aggregating, for each linguistic rule of the matched linguistic rules, the obtained profile of one or more dimension scores to obtain a corresponding intensity indication for the corresponding emotio-cognition of the linguistic rule:

determining a particular emotio-cognition satisfying a predetermined criteria, based on the obtained intensity indications; and displaying, by a display, the received natural language content together with the determined particular emotio-cognition and the corresponding intensity indication of the particular emotio-cognition, wherein new rules are generated and added to the rule-based engine by training, in parallel, an unsupervised learning engine and a supervised learning engine in multiple training epochs to identify, in natural language data items, a certain emotio-cognition, and determine an intensity of the certain emotio-cognition, wherein each training epoch of the unsupervised learning engine provides rule suggestions to subsequent training epochs of the rule-based engine, and in each training epoch, the rule-based engine provides scoring data to subsequent epochs of the unsupervised learning engine and the supervised learning engine.

* * * * *